United States Patent
Fujisawa et al.

(10) Patent No.: US 7,407,766 B1
(45) Date of Patent: Aug. 5, 2008

(54) SCREENING METHOD FOR AGONISTS OR ANTAGONISTS OF SEMAPHORIN 6C BY DETERMINING THE EFFECT OF A TEST COMPOUND ON THE INTERACTION BETWEEN SEMAPHORIN 6C AND PLEXIN-A1

(75) Inventors: Hajime Fujisawa, Kasugai (JP); Toru Kimura, Kusatsu (JP); Kaoru Kikuchi, Takarazuka (JP); Yasunori Murakami, Kobe (JP)

(73) Assignees: Japan Science and Technology Agency, Kawaguchi-shi, Saitama (JP); Dainippon Sumitomo Pharma Co., Ltd., Chuo-ku, Osaka-shi (JP)

( * ) Notice: Subject to any disclaimer, the term of this patent is extended or adjusted under 35 U.S.C. 154(b) by 716 days.

(21) Appl. No.: 10/148,409

(22) PCT Filed: Nov. 27, 2000

(86) PCT No.: PCT/JP00/08329

§ 371 (c)(1),
(2), (4) Date: May 30, 2002

(87) PCT Pub. No.: WO01/40457

PCT Pub. Date: Jun. 7, 2001

(30) Foreign Application Priority Data

Nov. 30, 1999 (JP) ................................ 11-341337

(51) Int. Cl.
*G01N 33/53* (2006.01)
*C12P 21/06* (2006.01)
*C12N 5/00* (2006.01)
*C12N 5/02* (2006.01)
*C12N 15/00* (2006.01)

(52) U.S. Cl. ........................ 435/7.2; 435/7.9; 435/69.1; 435/320.1; 435/325

(58) Field of Classification Search ........................ None
See application file for complete search history.

(56) References Cited

U.S. PATENT DOCUMENTS

2003/0077669 A1* 4/2003 Kimura et al. ................ 435/7.2

FOREIGN PATENT DOCUMENTS

EP 0 960 937 A1 12/1999

OTHER PUBLICATIONS

Castellani et al. Curr. Opin. Neurobiol. 2002. 12:532-541.*
Pawson et al. 2003, Science 300:445-452.*

Kaoru Kikuchi et al., "Cloning and Characterization of a Nvel Class VI Semaphorin, Semaphorin Y," Molecular and Cellular Neurosciences, vol. 13, 1999, pp. 9-23, XP002936786.

E. Maestrini et al., "A Family of Transmembrane Proteins with Homology to the MET-Hepatocyte Growth Factor Receptor," National Acad. Science of the USA, Jan. 23, 1996, vol. 93, No. 2, pp. 674-678, XP002285500 and XP002285502.

Hiroaki Kobayashi et al., "A Role for Collapsin-1 in Olfactory and Cranial Sensory Axon Guidance," The Journal of Neuroscience, Nov. 1, 1997, vol. 17, No. 21, pp. 8339-8352, XP002285501.

Britta J. Eickholt et al., "Structural Features of Collapsin Required for Biological Activity and Distribution of Binding Sites in the Developing Chick," Molecular and Cellular Neurosciences, vol. 9, No. 5-6, pp. 358-371, XP001196926.

Stefania Artigiani et al., "Plexins, Semaphorins, and Scatter Factor Receptors: A Common Root for Cell Guidance Signals?," IUBMB Life, Taylor and Francis, London, GB, vol. 48, No. 5., Nov. 1999, pp. 477-482, XP009007733.

Semaphorin Nomenclature Committee, "Unified Nomenclature for the Semaphosins/Collapsins," Cell Press, Cambridge, NA, US, vol. 97, 1999, pp. 551-552, XP001010231.

Jinhong Fan et al., "Localized Collapsing Cues Can Steer Growth Cones without Including Their Full Collapse", Neuron, vol. 14, 263-274, Feb. 1995.

E. Maestrini et al., "family of transmembrane proteins with homology to the MET-hepatocyte growth factor receptor", Proc. Natl. Acad. Sci. USA, vol. 93, pp. 674-678, Jan. 1996, Genetics.

Tatsuo Fukruyama et al., "Identification of a Novel Transmembrane Semaphorin Expressed on Lymphocytes", The Journal of Biological Chemistry, 1996, pp. 33376-33381.

Shin Takahashi, ("A Study on the Formation of Neural Networks and Its Mainteannce Mechanism") Kouji Nou Kinou No Bunshi Kinou Kamei Ni Muketa Kiban Gijutsu No Kkaihatsu Ni Kansu Kenkyu, 1995-1997.

(Continued)

Primary Examiner—Christine J. Saoud
Assistant Examiner—Chang-Yu Wang
(74) Attorney, Agent, or Firm—Venable LLP; Robert Kinberg; Ann S. Hobbs

(57) ABSTRACT

The present invention provides screening methods for agonists or antagonists of Sema6C using Plexin-A1, and tools for the screening and the like. It evaluates a case of making a recombinant protein having an extracellular domain of Semaphorin 6C contact a protein having an extracellular domain of Plexin-A1 by comparing it with a case of contacting a recombinant protein and a target substance having an extracellular domain of Semaphorin 6C, or the target substance with a protein having an extracellular domain of Plexin-A1. The evaluation will be carried out by the connectivity of a protein having an extracellular domain of Semaphorin 6C, a growth cone collapse activity of Plexin-A1 expressing cell, or a contractile activity of Plexin-A1 expressing cell.

12 Claims, 7 Drawing Sheets

OTHER PUBLICATIONS

Pengnian Lin et al., Inhibition of Tumor Growth by Targeting Tumor Endothelium Using a Soluble Vascular Endothelial Growth Factor Receptor.

Bernie Scallon et al., "Binding and Functional Comparisons of Two Types of Tumor Necrosis Factor Antagonists".

Genbank Accession No. AB000817, Mar. 24, 1999.
Genbank Accession No. AB014074, Mar. 20, 1999.
Genbank Accession No. AB013729, Mar. 20, 1999.
Genbank Accession No. D86948, Mar. 31, 2000.
Genbank Accession No. X87832, Sep. 10, 2004.

* cited by examiner

SCREENING METHOD FOR AGONISTS OR ANTAGONISTS OF SEMAPHORIN 6C BY DETERMINING THE EFFECT OF A TEST COMPOUND ON THE INTERACTION BETWEEN SEMAPHORIN 6C AND PLEXIN-A1

TECHNICAL FIELD

The present invention is based on a finding that a receptor for Semaphorin 6C (hereafter, abbreviated as Sema6C) is Plexin-A1. More specifically, the present invention relates to screening methods for agonists or antagonists for Sema6C using Plexin-A1, and screening tools for the screening and the like.

BACKGROUND OF THE INVENTION

Semaphorins constitute a large family of more than 20 kinds of secretory and transmembrane proteins, and are classified into 8 classes (Cell 97, 551-552, 1999). Many of the semaphorins function as a chemorepellent or an attractant against nerves, and regulate the guidance of axons, nerve fiber fasciculation and branching, and synaps formation. (For overview, see Annu. Rev. Neurosci. 19, 341-377, 1996, Science 274, 1123-1133, 1996). In particular, it has shown that Class 3 secretory semaphorins have strong activities of growth cone collapse and against axons of dorsal root ganglion (DRG) neurons or sympathetic ganglion neurons. (Cell 75, 217-227, 1993, Cell 75, 1389-1399, 1993, Neuron 14, 263-274, 1995, Neuron 14, 949-959, 1995, Neuron 14, 941-948, 1995, Eur. J. Neurosci. 8, 1317-1321, 1996, Neuron 18, 193-207, 1997).

It has been shown that Neuropilins (Neuropilin-1 and Neuropilin-2) bind to Class 3 Semaphorins (Neuron 19, 547-559, 1997, Cell 90, 739-751, 1997, Cell 90, 753-762, 1997). It is also known that by inactivating Sema3A (previously, Semaphorin D, a member of Class 3 Semaphorin) gene (Neuron 19, 519-530, 1997) or Neuropilin-1 gene (Neuron 19, 995-1005, 1997) in the mouse by targeted gene disruption, the abnormal guidance of peripheral nervous fibers or the induction of dendrite formation were recognized, and Neuropilin-1 is necessary for transmitting chemical reactive signals induced in Sema3A.

On the other hand, Plexin is a membrane glycoprotein, that has originally been identified in *Xenopus* tadpole nervous tissue (Dev. Biol. 122, 90-100, 1987, Neuron 9, 151-161, 1992, Neuron 14, 1189-1199, 1995). Several kinds of Plexins have been identified in various animals, which have been classified into 4 subfamilies, that is, Plexin-A, -B, -C and -D (Cell 99, 71-80, 1999). In mice or human, at least 3 kinds of Plexin belonging to Plexin A subfamily, that is, Plexins A1, A2 and A3 have been identified [previously Plexins-1, -2 and -3 in the mice respectively (Biochem. Biophys. Res. Commun. 226, 396-402, 1996, Biochem Biophys. Res. Commun. 226, 524-529, 1996), and NOV, OCT and SEX in the human, respectively (Proc. Natl. Acad. Sci. USA 93 674-678, 1996)]. An ectodomain (extracellular domain) of Plexin A subfamily has repeats of three units of a cysteine cluster similar to cysteine-rich domain present in c-Met and Met-related receptor protein tyrosine kinases [they are called C1, C2 and C3 (Neuron 14, 1189-1199, 1995) or Met-related sequence (MRS; Proc. Natl. Acad. Sci. USA 93, 674-678, 1996) (for overview, see Proc. Natl. Acad. Sci. USA 93, 674-678, 1996; Dev. Neurosci. 19, 101-105, 1997). Further, the approximately 500 amino acids (aa) residues between the N-terminal of Plexin and the first cysteine cluster is significantly homologous to Sema domains shared by Semaphorin family (Cell 75, 217-227, 1993, Cell 75, 1389-1399, 1993, Trends Cell Biol. 6, 15-22, 1996, Eur. J. Neurosci. 8, 1317-1321, 1996).

Our previous studies using *Xenopus* has shown that Plexin is expressed in neurons constituting specific nervous domains such as the optic tecum (Dev. Biol. 122, 90-100, 1987), inner plexiform layer of the retina and photoreceptor cells (Neuron 9, 151-161, 1992) the olfactory system, the lateral neural circuit, and the auditory equilibrium system (Neuron 14, 1189-1199, 1995), and suggested that Plexins are involved in neuron cell contact (Neuron 14, 1189-1199, 1995), nervous fiber guidance and fasciculation (J. Neurosci. 15, 942-955, 1995), or organization of the inner plexiform layer of the retina (Neuron 9, 151-161, 1992). However, the molecular nature of Plexins and its role in the development of a nervous system are not understood well.

Some recent studies show that Plexins function as receptors for semaphorins. Plexin-C1 (VESPR), which has two cysteine clusters rather than three in an ectodomain is expressed in cells derived from the lymphatic system, and is used as a receptor for SemaVA, a Class V Semaphorin encoded and secreted by Poxvirus (A39R; Immunity 8, 473-382, 1998). A research on Drosophila (Cell 95, 903-916, 1998) show that Plexin A is used as a receptor transmitting chemorepulsive signals induced by Sema-1a, a Class 1 Semaphorin, and is shown that it regulates the nervous fiber fasciculation in CNS or motor neurons.

A recent study on the interaction between Plexins and Semaphorins (Cell 99, 71-80, 1999) elucidates that Sema4D, a Class 4 Semaphorin, binds to Plexin-B1, Sema7A, a Class 7 Semaphorin (GPI anchor-type) binds to Plexin C1. Further, members of Plexin-A subfamily (Plexin-A1 and Plexin-A3) form a complex with neuropilins (Neuropilin-1 and Neuropilin-2), and transmit Sema3A signals, a Class 3 Semaphorin, into cells (Cell 99, 59-69, 1999, Cell 99, 71-80, 1999). All these insights suggest a possibility that Plexins are receptor molecules crucial to transmit some semaphorin signals independent of Neuropilins. However, since Semaphorins have various structures and functions, receptors for Semaphorins and their the signal transmission mechanisms may vary, depending on the Semaphorin classes. At present, the receptors of Class 6 Semaphorins have not been identified yet, and their relationships with Plexins have not been elucidated.

The present invention is based on the insight that a receptor for Sema6C, a member of Class 6 Semaphorin, is Plexin-A1, and the object of the present invention is to provide screening methods for agonists or antagonists of Sema6C using Plexin-A1, and tools for the screening. Since Sema6C has the growth cone collapse activity against nerve cells and cell contraction activity, screening methods in the present invention are useful for selecting therapeutic agents or preventive agents for patients by promoting or inhibiting these activities.

The present inventors produced a transfectant expressing Plexin-A, and keenly screened a ligand which is a Plexin-A subfamily member using this. As a result of this, we found that a Class 6 transmembrane Semaphorin, a Sema6C (SemaY; Mol. Cell. Neurosci. 13, 9-23, 1999, SEQ ID NOS:8-10) specifically binds to Plexin-A1, and the recombinant proteins of the ectodomain (extracellular domain) of Sema6C induce contraction of fibroblasts or collapse of growth cones in the nerve cells, that express Plexin-A1, and we demonstrated that a receptor of a transmembrane semaphorin Sema6C is Plexin-A1. Accompanied by finding that a receptor of a Sema6C is Plexin-A1, it became possible to screen agonists or antagonists of Sema6C using Plexin-A1.

It is well known that Sema6C has a growth cone collapse activity (WO98/11216 pamphlet, Moll. Cell. Neurosci. 13, 9-23, 1999), and it is shown that the screening of antagonists of Sema6C is useful in developing promoting agents for neural regeneration (WO 98/11216 pamphlet). In the present invention, since a receptor for Sema6C is identified, it became possible to perform more effective and highly specific screening using Plexin-A1.

In particular, since Sema6C binding sites and Plexin-A1 are localized to the auditory system, and Sema6C has a growth cone collapse activity, the Sema6C is considered to be relevant to the suppression of auditory nerve elongation or the collapse of growth cone. The Sema6C is also considered to be relevant to the suppression of olfactory nerve elongation or the collapse of their growth cones. Therefore, the screening methods in the present invention is useful in screening for a therapeutic agents or preventive agents for various neural diseases, in particular auditory and/or olfactory nervous diseases. Since Sema6C also a cell contraction activity, the screening methods in the present invention can be used to screen agents that suppress or enhance cell migration using the contraction of cells expressing Plexin-A1 as an index. The methods can be used to screen therapeutic agents or preventive agents for the promotion of blood vessel formation migration of marignant cells.

Further, the present invention specifically has shown for the first time that Plexin-A1 is specifically expressed in the auditory neurons (all ganglia and nuclei constituting to auditory pathway). Therefore, the antisense strands of DNA/RNA encoding Plexin 1 or the antibodies against Plexin-A1 can be used for diagnosing auditory or olfactory nervous diseases.

Based on the insights mentioned above, the present invention has been completed.

DISCLOSURE OF THE INVENTION

The present invention relates to a screening method for agonists or antagonists for Semaphorin 6C, comprising a step of making a protein with an extracellular domain of Plexin-A1 contact with a target substance in vitro (claim 1), the screening method for agonists or antagonists for Semaphorin 6C according to claim 1, comprising a step of comparing and evaluating (i) a case of making a recombinant protein with an extracellular domain of Semaphorin 6C contact with a protein having an extracellular domain of Plexin-A1 with (ii) a case of making a recombinant protein with an extracellular domain of Semaphorin 6C and a target substance, or a target substance contact with a protein having an extracellular domain of Plexin-A1 (claim 2), the screening method for agonists or antagonists for Semaphorin 6C according to either of claim 1 or 2, wherein the protein having an extracellular domain of Semaphorin 6C is a protein bound to a marker protein and/or a peptide tag (claim 3), the screening method for agonists or antagonists for Semaphorin 6C according to claim 3, wherein the marker protein is alkaline phosphatase or an immunoglobulin Fc domain (claim 4), the screening method for agonists or antagonists for Semaphorin 6C according to any of claims 1 to 4, wherein a cell membrane or a cell expressing a protein with an extracellular domain of Plexin-A1 is used (claim 5), the screening method for agonists or antagonists for Semaphorin 6C according to claim 5, wherein a cell membrane or a cell expressing a protein having an extracellular domain of Plexin-A1 is a transformed cell wherein the DNA encoding a protein having an extracellular domain of Plexin-A1 is preserved in a stable manner (claim 6), the screening method for agonists or antagonists for Semaphorin 6C according to any of claims 1 to 6 wherein the protein having an extracellular domain of Plexin-A1 is a recombinant protein (claim 7), the screening method for agonists or antagonists for Semaphorin 6C according to any of claims 1 to 7, wherein the protein having an extracellular domain of Plexin-A1 is Plexin-A1 (claim 8), the screening method for agonists or antagonists for Semaphorin 6C according to any of claims 2 to 8, comprising a step of detecting the presence or absence of a signaling arising from an interaction between a protein having an extracellular domain of Semaphorin 6C and a protein having an extracellular domain of Plexin-A1 (claim 9), the screening method for agonists or antagonists for Semaphorin 6C according to claim 9, wherein the signaling is a connectivity of a protein having an extracellular domain of Semaphorin 6C against a protein having an extracellular domain of Plexin-A1, a growth cone collapse activity, or a contractile activity of a Plexin-A1 expressing cell (claim 10), a screening method for agonists or antagonists for Semaphorin 6C, comprising a step of injecting a target substance to non-human animals and evaluating Plexin-A1 activity (claim 11), a screening method for agonists or antagonists for Semaphorin 6C comprising a step of injecting a target substance to non-human animals whose gene function encoding Plexin-A1 is lacked or excessively expressed on the chromosome, and evaluating the Plexin-A1 activity (claim 12), a screening method for agonists or antagonists for Semaphorin 6C, wherein the target substance is injected to non-human animals whose gene function encoding Plexin-A1 is lacked or excessively expressed on the chromosome, and its Plexin-A1 activity is assessed and compared with that of wild-type non-human animals (claim 13), the screening method for agonists or antagonists for Semaphorin 6C according to any of claims 11 to 13, wherein the Plexin-A1 activity is a growth cone collapse activity against a neural cell or a contractile activity against cells (claim 14), the screening method for agonists or antagonists for Semaphorin 6C according to any of claims 11 to 14, wherein the non-human animals are mice or rats (claim 15), an agonist or for Semaphorin 6C obtainable by a screening method for agonists or antagonists for Semaphorin 6C according to any of claims 1 to 15 (claim 16), a pharmacological composition comprising the agonists or antagonists for Semaphorin 6C according to claim 16 as an active agent (claim 17), the pharmacological composition according to claim 17, useful as an agent for treating and/or preventing auditory and/or olfactory nervous diseases (claim 18), a migration-inhibition agent or migration-enhancement agent of Plexin-A1 comprising the agonists or antagonists for Semaphorin 6C according to claim 16 as an active agent (claim 19), a fusion protein wherein a protein having an extracellular domain of Class 6 Semaphorin is bound with a marker protein and/or a peptide tag (claim 20), the fusion protein according to claim 20, wherein a Class 6 Semaphorin is Semaphorin 6C (claim 21), the fusion protein according to either of claim 20 or 21, wherein the marker protein is alkaline phosphatase or an immunoglobulin Fc domain (claim 22), a transformant wherein DNA encoding a protein having an extracellular domain of Plexin-A1 is preserved stably (claim 23), a probe used for diagnosing central nervous diseases, comprising whole or part of an antisense strand of DNA or RNA encoding Plexin-A1 (claim 24), the probe used for the diagnosis according to claim 24, wherein the central nerve is an auditory nerve (claim 25), a medicine used for diagnosing central nervous diseases, comprising the diagnostic probe according to claim 24 or an antibody to Plexin-A1 (claim 26), the medicine used for diagnosing auditory nervous diseases according to claim 26, wherein a central nerve is an auditory nerve (claim 27), a screening method for agents inhibiting or promoting the expression of Plexin-A1, comprising steps of culturing in vitro a cell expressing a protein having an extracellular domain of Plexin-A1 in the presence of the target substance and measuring and evaluating the amount of Plexin-A1 expression in the cell (claim 28), a screening method for agents inhibiting or promoting the expression of Plexin-A1, comprising steps of culturing in vitro a cell obtained from non-human animals whose gene function encoding Plexin-A1 is lacked or is excessively expressed in the presence of a target substance, and measuring and evaluating the amount of Plexin-A1 expression in the cell (claim 29), a screening method for agents inhibiting or promoting the expression of Plexin-A1, comprising steps of injecting a target substance to non-human animals, and measuring and evaluating the amount of Plexin-A1 expression (claim 30), a screening method for agents inhibiting or promoting the expression of Plexin-A1, comprising steps of injecting a target substance to non-human animals whose gene function encoding Plexin-A1 is lacked or excessively expressed on the chromosome, and measuring and evaluating the amount of Plexin-A1 expression (claim 31), a screening method for agents inhibiting or promoting the expression of Plexin-A1, comprising steps of injecting a target substance to non-human animals whose gene function encoding Plexin-A1 is lacking or excessively expressed on the chromosome, and measuring and evaluating the amount of Plexin-A1 expression with that of wild-type non-human animals (claim 32), the screening method for agents inhibiting or promoting the expression of Plexin-A1 according to any of claims 29 to 32 wherein the non-human animal is mice or rats (claim 33), an agent inhibiting or promoting the expression of Plexin-A1, obtained by the screening methods for an agent inhibiting or promoting the expression of Plexin-A1 according to any of claims 28 to 33 (claim 34), and a pharmacological composition comprising the agent inhibiting or promoting the expression of Plexin-A1 according to claim 34 as an active agent (claim 35).

BEST MODE TO CARRY OUT THE INVENTION

Figure 1:
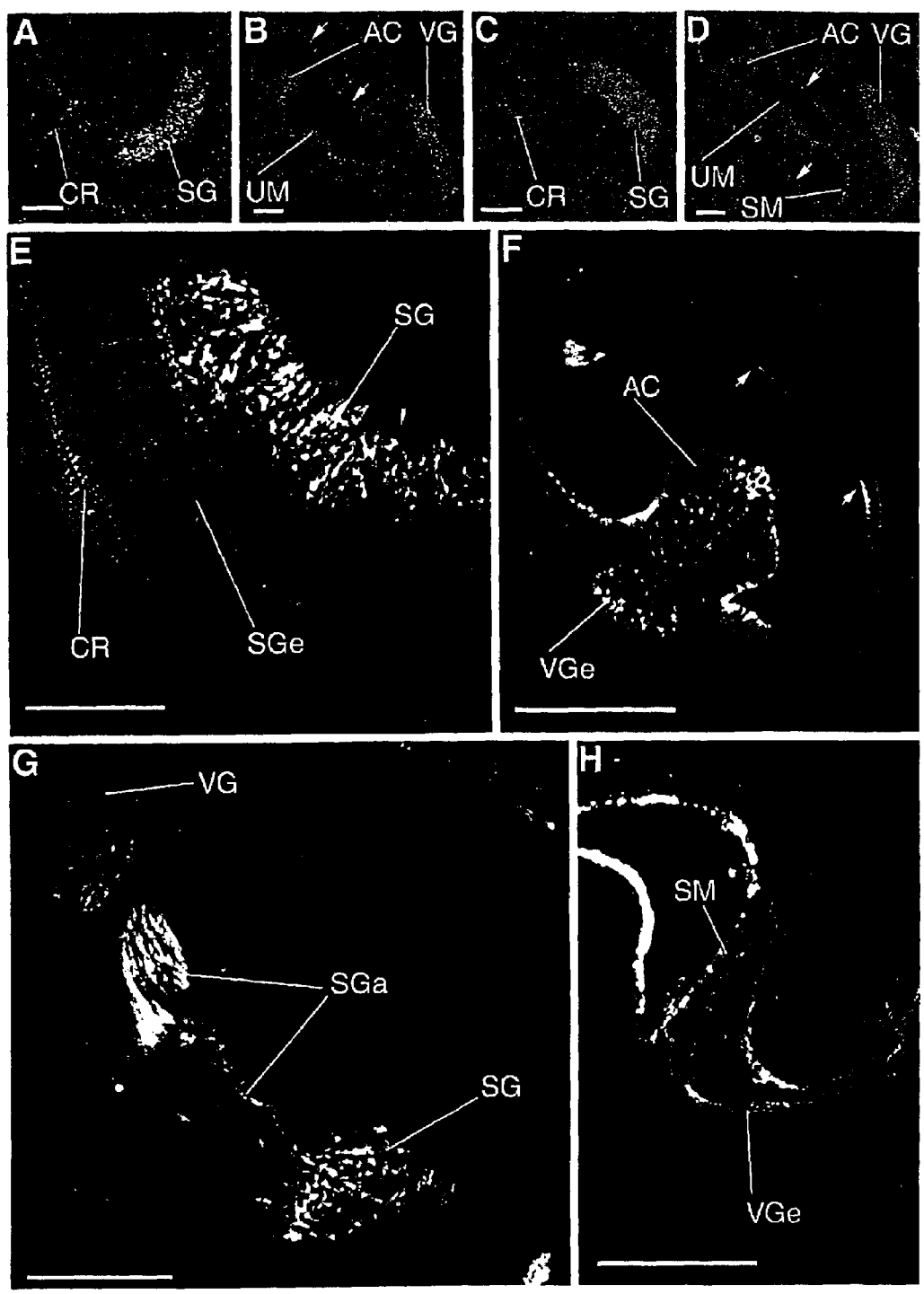
FIG. 1 shows the results of expressing Plexin-A1 and Plexin-A3 in the inner ears by in situ hybridization and immunostaining.

"A protein having an extracellular domain of Plexin-A1" used for screening agonists or antagonists of Sema6C in the present invention may be either a natural type or a recombinant. Further, although Plexin-A1 is preferably human-type, Plexin-A1 derived from other species such as mouse-type can be used for the same purpose. The sequence of amino acids and the sequence of bases in mouse-type Plexin-A1 are published in the reference (Biochem. Biophys. Res. Comm. 226, 524-529, 1996) or as Genbank accession No: D86948 (SEQ ID NO:6). Further, the sequences of human Plexin-A1 are published in the reference (Cell 99, 71-80, 1999) or as Genbank accession No: X87832 (SEQ ID NO:5), and it is easy to clone using these sequencing information.

Although the "extracellular domain" of Plexin-A1 refers to the part of the 1st to the 1237th in the sequence of amino acids in Plexin-A1 in the reference, or the part comprising the sequence of amino acids having this part and 10 or less of residues of amino acids in a forward or backward direction, a sequence of amino acids comprising modifications such as substitution, deletion, addition is also included in the "extracellular domain" of Plexin-A1, as long as the ability of binding to Sema6C is maintained.

The "protein having an extracellular domain in Plexin-A1" in the present invention refers to part or whole of the proteins of Plexin-A1 having at least the extracellular domain. Since Sema6C binds to an extracellular domain of Plexin-A1, which is a receptor, it can play a role of Plexin-A1 in the screening of the present invention as long as it has the extracellular domain. Preferably, a whole protein of Plexin-A1 is used. Further, not only the natural type but also the one whose part of the amino acid sequence is mutated is induced in the category of the "protein having an extracellular domain of Plexin-A1" as long as it maintains the ability to bind to Sema6C.

The DNA encoding a protein having part or whole of Plexin-A1 (henceforth, it may be abbreviated as DNA of Plexin-A1 for short, and the expressed product by the DNA may be abbreviated simply as protein of Plexin-A1 for short) can be cloned by using cDNA library and the like derived from human or animal brains with an appropriate part of DNA as probes for hybridization or primers for PCR based on the sequence information set forth in the reference (Cell 99, 71-80, 1999 or Genbank accession No: X87832, SEQ ID NO:5). The cloning can easily be performed by the people skilled in the art, following introductory books such as Molecular Cloning 2nd Edt., Cold Spring Harbor Laboratory Press, 1989). Further, the mutation can easily be performed by the people skilled in the art, based on introductory books such as Molecular Cloning 2nd Edt., Cold Spring Harbor Laboratory Press 1989, PCR A Practical Approach, IRL Press p 200, 1991). The mutation can preferably be in the domain except for the extracellular domain of Plexin-A1, and preferably be substituted to conserved amino acids.

As a technique for expressing protein from the DNA obtained in the above-mentioned method, the method mentioned below can be exemplified. That is, firstly the DNA of Plexin-A1 prepared beforehand is inserted into a known expressing vector such as pCAGGS (Gene 108, 193-199, 1991) or pcDNA1.1, pcDNA3.1 inducer (Invitrogen). At the time, it is preferred that it comprises a Kozaks sequence before the first ATG of Plexin-A1. It is possible to produce a transformant which expresses proteins of the Plexin-A1 corresponding to the DNA of the introduced Plexin-A1 on the surface of cells by introducing the product to an appropriate host cell after that. Further, some kinds of the DNA of the used Plexin-A1 can secrete the Plexin-A1 protein in the culture supernatant (for example, in the case of using the DNA encoding only an extracellular domain). Although as a host, L cell, which is a mammal cell strain generally and widely-spread, CHO cell, C127 cell, BHK21 cell, BALB/c3T3 cell (including the mutant strains where dihydrofolic acid reductase and thymidine kinase are lacking) or COS cell, there is no such restriction, and insect cells, yeasts or bacteria can also be used.

A method of introducing the Plexin-A1 expressing vector into a host cell can be any method of introducing as long as it is a method of introducing a well-known vector into a host cell, and can be exemplified by a method using calcium phosphate transfection (J. Virol. 52, 456-467, 1973), a method using LT-1 (Panvera), transfection lipids (Lipofectamine, Lipofection; Gibco-BRL) and the like.

As for the transformants wherein the transferred genes are conserved in a chromosome of an animal cell in a stable manner (so-called stable transformant), there are a number of cases where they are difficult to obtain, depending on the kinds of transfected genes, and as for Plexin-A1, there are no known examples of obtaining a stable transformant. We attempted a variety of results such as adjusting methods of recombinant cells in the present invention, and we succeeded for the first time to obtain a transformant conserving the DNA of Plexin-A1 in a stable manner.

The transformant wherein Plexin-A1 is expressed on the surface of a cell obtained as mentioned above can be used for the screening system with no modification as mentioned below, and in the case where cell membranes of the transformant are used for screening, for example, a cell membrane can be prepared as mentioned below. That is, a precipitation of a cell membrane fraction is obtained by first adding hypotonic homogenate buffer (10 mM of tris-hydrochloride, 1 mM of EDTA, 0.5 mM of PMSF or 1 mM of AEBSF, 5 μg/ml of aprotinin, 5 μg/ml of leupeptin; pH7.4) and leave it for about 30 min. at 4° C. to destroy the cells hypotonically, then homogenize them by pipetting, and centrifugate for 30 min. at 50,000×g at 4° C. to obtain precipitation. Further, cell membrane fractions of the present invention can be obtained by suspending the precipitation into tris-hydrochloride buffer physiological saline solution (tris-hydrochloride, 154 mM of sodium chloride; pH7.4).

The cell membrane fractions of the present invention can be obtained by such methods as in F. Pietri-Rouxel (Eur. J. Biochem., 247, 1174-1179, 1997).

Further, as described below, there are cases where Plexin-A1 which is isolated can be used for screening by itself, and the transformants obtained as mentioned above or Plexin-A1 isolated from the cell membrane fractions can be used in such cases. More concretely, crude extracts containing Plexin-A1 can be obtained by a method described in R. G. Shorr et al. (Proc. Natl. Acad. Sci. USA, 79, 2778-2782, 1982, J. Biol. Chem. 257, 12341-12350, 1982) and others. Further, as a method of purifying Plexin-A1 from the crude extracts, it can be a method in J. L. Benovic et al. (Biochem., 23, 4510-4518, 1984).

Still further, Plexin-A1 can be purified by a normal method from a culture supernatant in the case where Plexin-A1 (for example, an extracellular domain of Plexin-A1) is secreted from a transformant, as described above, for example using a column bound to an anti-Plexin-A1 antibody, and in the case where normal peptide tags are added to an extracellular domain of Plexin-A1, using a column bound to a substance having affinity with this tag.

Sema6C of the present invention used to be called SemaY (Semaphorin Y) once, the sequences of bases and of the sequences of amino acids of rat-(SEQ ID NO:8 and SEQ ID NO:9) and human-type (SEQ ID NO:7) are disclosed in International Publication No: 98/11216 pamphlet and Moll. Cell. Neurosci. 13, 9-23, 1999. Sema6C has a splicing isoform where 96 base pairs in the extracellular domain are not deleted, and it has been shown that both the isoform (Sema6C-L) and the isoform where 96 base pairs are deleted (Sema6C-S) have an activity (growth cone collapse activity) (International Publication No: WO98/11216 pamphlet and Moll. Cell. Neurosci. 13, 9-23, 1999). Therefore, it is possible to use one or both of the two isoforms for the screening. Further, a modified protein undergoing modification such as substitution or deletion of the sequence of amino acids can be used, as long as it has essentially the same characteristics as Sema6C.

As described below, in the screening of the present invention, the protein comprising an extracellular domain of Sema6C can be used as a control to measure the activity of the target substance. Further, since an extracellular domain of Sema6C binds to an extracellular domain of Plexin-A1, it serves as Sema6C in the screening of the present invention as is the case of Plexin-A1, as long as it has at least an extracellular domain of Sema6C.

Although an "extracellular domain" of Sema6C here refers to a portion of a sequence of the 1st to the 599th amino acids in Sema6C in the reference, or a portion of a sequence of amino acids which comprise the portion and 20 or less of its forward or backward residues of the amino acids, the one containing recombination such as substitution, deletion, addition and others is included in the domain of "extracellular domain" of Sema6C, as long as it has the activity of binding to Plexin-A1, the growth cone collapse activity, and/or it has a cell contraction.

A "protein having an extracellular domain of Sema6C" in the present invention refers to part or whole of proteins of Sema6C having at least the extracellular domain part. Further, not only a natural type but also the one wherein part of the sequence of amino acids are recombinant such as substitution, deletion, and addition is included in the category of the "protein having an extracellular domain of Sema6C", as long as it is possible to bind to Plexin-A1.

The DNA encoding a protein having part or whole of Sema6C can be cloned by using cDNA library derived from a brain or a muscle and the like, using appropriate portions of DNA as a probe for hybridization or as a primer for PCR, based on the sequence information disclosed in International Publication No: 98/11216 pamphlet and Moll. Cell. Neurosci. 13, 9-23, 1999. Such cloning can easily be performed by a person in the art, following an introductory book such as Molecular Cloning 2nd Edt., Cold Spring Harbor Laboratory Press 1989 and others. Further, such a recombination can easily be performed by a person in the art, following an introductory book such as Molecular Cloning 2nd Edt., Cold Spring Harbor Laboratory Press, 1989, PCR A Practical Approach IRL Press p 200, 1991 and others. Such a recombination is preferably be performed in the part other than the extracellular domain of Sema6C, and further, substitution to conserved amino acids is preferable.

As a method to express proteins from the DNA obtained in a way mentioned above, the same method used for Plexin-A1 mentioned above can be used as well.

To perform the screening of the present invention more simply, the present inventors, as a result of various attempts, produced a fusion protein wherein a marker protein and/or a peptide tag are/is bound to a protein having an extracellular domain of Sema6C, and found that the fusion protein shows a conservation of a biological activity as well as a clear binding to Plexin-A1 and that it can eligbly be used as a screening tool of the present invention. Such a fusion protein mentioned above, especially in a case of a protein whose tertiary structure is unclear, is difficult to obtain due to the problems such as the lack of the amount of the expression in a transformed cell, the lost of biological activity, the decline of stability and others caused by the fact that the protein is a fusion protein, the production of the fusion protein has never been succeeded with respect to Sema6C or with respect to any of Class 6 Semaphorin to which Sema6C belongs.

Since the present invention showed that a fusion protein of a protein having an extracellular domain of Sema6C is obtained, the fusion protein binds to Plexin-A1, which is a receptor, and it conserves biological activity, as described above, such fusion proteins can be produced with members of Class 6 Semaphorin (Sema6A, Sema6B) other than Sema6C following the description set forth in the specification, and it is evident that the fusion protein can bind to the receptor. Therefore, the present invention is to provide a fusion protein wherein an extracellular domain of Class 6 Semaphorin are bound together with a marker protein and/or a peptide tag.

As a marker protein refers to here, any well-known marker protein can be exemplified by, for example, alkaline phosphatase (Cell 63, 185-194, 1990), Fc region of an antibody (Genbank accession number M87789), HRP and others. Among others, alkaline phosphatase is the most preferable.

A "peptide tag" is exemplified by well-known peptide tags such as Myc tag (Glu-Gln-Lys-Lue-Ile-Ser-Glu-Glu-Asp-Ile) (SEQ ID NO: 1), His tag (His-His-His-His-His-His) (SEQ ID NO: 2), FLAG tag (Asp-Tyr-Lys-Asp-Asp-Asp-Asp) (SEQ ID NO: 3).

Furthermore, the one wherein a marker protein or a peptide tag is bound to an extracellular domain of Class 6 Semaphorin mentioned above is useful not only for screening but also as a marker for diagnosing nervous abnormality (especially a marker for diagnosing auditory nervous abnormality), and as a reagent used for research in the field.

An "agonist of Sema6C" in the present invention refers to a substance that binds to Sema6C and/or Plexin-A1, which is a receptor, and affects a downstream signaling molecular to induce a Sema6C-like function by itself, or a substance that binds to Sema6C and/or Plexin-A1, which is a receptor, and affects a downstream signaling molecule to strengthen a function of Sema6C. Further, an "antagonist of Sema6C" in the present invention refers to a substance that inhibits a function of Sema6C by binding to Sema6C and/or Plexin-A1, which is a receptor, or affecting a downstream signaling molecule.

Methods for screening an agonist or an antagonist of Sema6C by using the screening tools mentioned above can roughly be classified into a method of making a protein having an extracellular domain of Plexin-A1 contact in vitro with a target material, and a method of injecting in vivo the subject substance to non-human animals, and each of them are explained below.

First, as a screening method for an agonist or an antagonist of Sema6C of the present invention characterized by making a protein having an extracellular domain of Plexin-A1 contact with an subject substance in vitro can concretely be illustrated by the following three methods:

1) Methods Using a Cell Wherein Plexin-A1 Protein is Expressed

As a method of performing a screening of the present invention using a cell expressing a protein having an extracellular domain of Plexin-A1 produced by the description mentioned above, the following illustrated methods can concretely exemplified.

That is, in screening for an antagonist following the description described above, Sema6C-S-AP, a fusion protein is produced from extracellular domain of Sema6C-S (short varaiant) and alkalin phoastphase (AP), together with following the above description. On the other hand, a transformant expressing Plexin-A1 protein on the surface of a cell is produced following the description mentioned above. Next, the connectivity of the Sema6C-S-AP to a cell is detected by alkaline phosphotase activity (i) when Sema6C-S-AP is added, and (ii) when Sema6C-S-AP or a target substance is added. In the cases where AP in (ii) has a lower the level of activity than that in (i), or shows no activity, it is shown that the target substance is an antagonist of Sema6C. See the examples for more detail. Further, it is possible to use as an index the fact that the target substance inhibits the change of a cell observed when Sema6C is added to the cell expressing Plexin-A1 protein, when the same experiment mentioned above is performed instead of the connectivity of Sema6C-S-AP to a cell expressing Plexin-A1 protein. A "change of a cell" used here refers to the growth core collapse or shrinkage and others.

Further, in screening for an agonist of Sema6C, the responses such as growth cone collapse, shrinkage of a cell shown by the cells expressing Plexin-A1 proteins are compared, for example, with a transformant wherein Plexin-A1 proteins are expressed on the surface of a cell, (i) when Sema6C-S-AP is added, and (ii) when a target substance is added or when Sema6C-S-AP and a subject substance are added. In the case where the same or similar responses are recognized in the case (i) and the case (ii) where only a target substance is added, it shows that the subject substance is an agonist of Sama6C. Further, in the case where a function of Sema6C is strengthened as observed when Sema6C-S-AP is added by adding the target substance, it is considered as an agonist. See the examples for more detail.

As a cell expressing Plexin-A1 protein, it is convenient to use a cell wherein a recombinant Plexin-A1 protein is expressed on the surface of a cell as mentioned above. However, since it is found from the present invention that nervous cells such as cultured inferior colliculus neuron or dorsal root ganaglion (DRG) neuron express Plexin-A1 proteins on the surface of the cell, such neural cells can be used for the screening in the present invention as well. For the culture of such cells, refer to International Publication WO98/11216 pamphlet or the examples described below.

There is no particular restrictions on a concrete method of detection, as long as the method can detect the presence or absence of signaling arising from the interaction between a protein having an extracellular domain of Sema6C and a protein having an extracellular domain of Plexin-A1. The screening of the present invention can performed by the measurement of the morphological changes of a cell (Cell 99, 59-69, 1999, see also the examples described below), and the measurement of the growth cone collapse (International Publication 98/11216 pamphlet and Moll. Cell. Neurosci. 13, 9-23, 1999, see also the examples described below), other than the cases where the connectivity of a protein having an extracellular domain of Sema6C against a protein having an extracellular domain of Plexin-A1 as described above.

2) Methods Using Cell Membranes Wherein a Plexin-A1 Protein is Expressed

Instead of using a cell wherein a protein having an extracellular domain of Plexin-A1 is expressed on the surface of a cell, the screening of the present invention can be performed by using a cell membrane prepared from the cell, following the same method as in section 1). In this case, the connectivity to a protein having an extracellular domain of Plexin-A1 is measured.

3) Methods Using a Protein Having an Extracellular Domain of Isolated and Purified Plexin-A1

The screening of the present invention can be performed using a protein having an extracellular domain of Plexin-A1 isolated and purified based on the description mentioned above. The connectivity to a protein having an extracellular domain of Plexin-A1 is measured in this case as well.

Next, a screening method for an agonist or an antagonist of Sema6C of the present invention characterized in that Plexin-A1 activity is evaluated by injecting a subject substance to non-human animals can concretely be exemplified by the following ways.

A method for screening an agonist or an antagonist of Semaphorin 6C can concretely be exemplified by injecting a target substance to wild-type non-human animals such as rats or mice, and/or non-human animals wherein a gene function encoding Plexin-A1 is deficient or excessively expressed on a chromosome, and evaluating or comparing/evaluating Plexin-A1 activities such as a growth cone collapse activity or a contractile activity against a cell.

In the present invention, non-human animals wherein a gene function encoding Plexin-A1 is deficient on a chromosome refers to non-human animals wherein part or whole of a gene function encoding Plexin-A1 becomes inactivated on a chromosome by gene recombination such as destruction/deficiency/substitution and the like, and the function of expressing Plexin-A1 is lost, and non-human animals wherein a gene function encoding Plexin-A1 is excessively expressed on a chromosome refers to non-human animals producing Plexin-A1 more massively than wild-type non-human animals. Further, although it can correctly be exemplified by non-human animals including rodents such as mice and rats as non-human animals in the present invention, it is not limited to these.

Further, since homozygote mice born following Mendel's laws include a type deficient of or a type excessively expressing the gene functions encoding Plexin-A1 and the wild-types born from the same mothers, and comparative experiments can be carried out precisely at the individual levels by using deficient-type and excessively expressive-type homozygote mice and their wild-type mice born from the same mothers, it is preferable to use wild-type non-human animals, that is, animals of the same type as non-human animals wherein a gene function encoding the Plexin-A1 is deficient or excessively expressed on a chromosome, further, it is preferable to use animals born from the same mother together, for example, in screening an agonist or an antagonist such as Sema6C. A method of producing non-human animals wherein a gene function encoding Plexin-A1 is deficient or excessively expressed on a chromosome is explained below using Plexin-A1 knockout mice or Plexin-A1 transgenic mice as an example.

A Plexin-A1 knockout mouse is specified by screening a gene encoding Plexin-A1 using a gene fragment obtained from a mouse gene library by PCR or other methods using DNA sequencing, and subcloning using a gene encoding screened Plexin-A1. A target vector is produced by replacing whole or part of a gene encoding Plexin-A1 in the close with pMC1 neo-gene cassette, and introducing a gene such as diphtheria toxin A fragment (DT-A) gene or thymidine kinase of herpes simplex virus (HSV-tk) on the 3' end.

The targeting vector prepared is linearized, introduced into an ES cell by electropolation and others, performed by homologous recombination, and the ES cells showing homologous recombination from the homologous recombinants by antibiotics such as G418 or gancyclovir (GANC) and the like. Further, it is preferable to confirm by the Southern blotting whether a selected ES cell is a target recombinant. The clones of the confirmed ES cells are microinjected into a mouse blastocyst, and the blastocyst is returned to a nursing parent to produce chimera mice. The chimeric mice are intercrossed with a wild-type mouse to obtain a heterozygote mouse, and the heterozygote mouse is intercrossed to produce a Plexin-A1 knockout mouse of the present invention. Further, a method of confirming whether the knockout mouse is produced can be the Northern blotting by isolating RNA from the mouse obtained by the above-mentioned method, or can be the Western blotting by examining the expression of the protein in the mouse.

As for a Plexin-A1 transgenic mouse, a transgene is constructed by fusing a chicken β actin, mouse neurofilaments, promoters such as SV40, and rabbit β-globin, polyA or intron of SV40 and others are fused to construct a transgene to microinject the transgene to a pronucleus of a mouse fertilized egg. After cultured in the obtained egg cells, the egg was transplanted to an oviduct of a nursing mouse, feed the transplanted animals after that, and is able to generate a transgenic mouse by selecting a baby mouse from having the cDNA from the born baby mice. Further, selection of a baby mouse having the cDNA can be carried out by extracting the crude DNA from a mouse tail and others and performed by a dot hybridization method using a probe as a Plexin-A1 introduced gene as a probe, or PCR and others using a specific primer.

Since Sema6C has an activity of suppressing nervous elongation and a growth cone collapse activity of axons (International Publication 98/11216 pamphlet), the agonist or antagonist of Sema6C selected using the screening method in the present invention mentioned above can be used as a pharmaceutical medicine or a preventive medicine for neurotics. That is, an antagonist for Sema6C can be used as a pharmaceutical or preventive medicine for neurotics by promoting nervous elongation, an agonist for Sema6C can be used as a pharmaceutical medicine or preventive medicine for neurotics by regulating nervous elongation. The screening method of the present invention is useful to select pharmaceutical medicine or preventive medicine for neurotics.

Specifically, as evident from the fact that the binding domain of Sema6C and Plexin-A1 are localized in accordance with an auditory nervous tissue, and Sema6C has the growth cone collapse activity against an auditory nerve, the Sema6C relates to suppression of elongation of auditory nerves and relates to collapse of growth cones. Therefore, the screening method in the present invention is effective for selection of a pharmaceutical medicine or a preventive medicine for auditory neurotics, and specifically a screening method for an antagonist for Sema6C can select a pharmaceutical medicine or a preventive medicine for the diseases with auditory neurotics by promoting the elongation of neurotics.

Further, since Plexin-A1 is expressed not only in auditory nerves but also olfactory nerves as described below, a screening method of the present invention can effectively be used for screening for pharmaceutical medicine or preventive medicine for olfactory neurotics.

Further, since it became evident that Sema6C had a shrinkage activity against a cell mediating Plexin-A1, a screening method of the present invention can also be used to select migration suppression agents or migration enhancement agent. An agonist for Sema6C obtained from the screening can be used, for example, as a pharmaceutical medicine or preventive medicine for the transfer of cancer by suppressing cell migration, and an antagonist for Sema6C can be used, for example, as an enhancing agent for the neogenesis of blood vessel by enhancing cell migration, using the shrinkage of a cell expressing Plexin-A1 as an index.

The present invention is to provide pharmaceutical medicines or preventive medicines for auditory and/or olfactory neurotics obtained by the screening methods, or migration-suppression agents or enhancement agents for cells expressing Plexin-A1, and more concretely, for example, it can be a low molecular compound obtained by performing the screening neutralizing antibody against Sema6C, recombinant proteins of Sema6C and low molecular compound library (International Publication WO98/11216 pamphlet).

The present invention also provides a probe for diagnosing a disease at the central nervous system, comprising whole or part of an antisense strand of DNA or RNA encoding Plexin-A1, and a diagnosing agent for a disease at the central nervous system comprising the probe.

As described in the examples below, the tissue distribution of Plexin-A1 was revealed for the first time in the present invention using the methods of in situ hybridization and immunostaining. That is, Plexin-A1 is specifically expressed in the nerves of the auditory systems (more concretely, the cochlear nervous, the ventral nucleus and dorsal nucleus, the upper olive nucleus group, the trapezoid body, the dorsal and ventral lateral lemniscus nuclei, the inferior colliculus, the medial geniculate body, the auditory area of the cerebral cortex), and Plexin-A1 is also expressed in the nerves of the olfactory systems (more concretely, the vomeronasal organ and sensory epithelium in the nasal cavity, mitral cells and granular cells in the olfactory bulb, the lateral olfactory striae, the amydogdaloidal nucleus). Therefore, the presence or absence of diseases and the status of the disease in progression can be detected in the nervous tissues mentioned above, especially in the auditory systems by performing in situ hybridization of Plexin-A1 against, for example, a pathological tissue.

There is no particular limitations as long as it is whole or part of an antisense strand of DNA or RNA (cRNA) encoding Plexin-A1, and it is has a length (at least 20 bases or more) enough to hold as a probe. More concretely, the part of position 564-2732 of the OFR of Plexin-A1 can be given as an example. To use the probe as an active component of a diagnosing agent, it is preferable to lyse it to appropriate buffers or aseptizd water in which a probe will not be decomposed. Further, as an in situ hybridization, it can, for example, be a method described in J. Neurobiol. 29, 1-17, 1996. It is also possible to adopt an in situ PCR method. Also refer to the examples described below.

In the diagnosis, not only a probe but also an antibody against Plexin-A1 can also be used, and immunostaining can be used in this case. (Dev. Biol. 170, 207-222, 1995; J. Neurobiol. 29, 1-17, 1996, see the examples described below). An antibody can be prepared by a method described, for example, in Antibodies; A Laboratory Manual, Lane, H. D. et al (eds.), Cold Spring Harber Laboratory Press, New York, 1989).

The present invention also provides screening methods for agents suppressing or enhancing Plexin-A1 expression or agents, by culturing in vitro together with a target substance the cells expressing proteins having an extracellular domain of Plexin-A1 or the cells obtained from non-human animals wherein a gene function encoding Plexin-A1 is lacked or is expressed excessively on chromosomes, then administrating the target substance to non-human animals and others wherein the cells expressing proteins having an extracellular domain of Plexin-A1 or the gene functions encoding Plexin-A1 are deficient or express excessively on chromosomes, and then measuring/evaluating an amount of expression of Plexin-A1. When administrating a target substance to non-human animals, it is possible to compare/evaluate a case of using wild-type non-human animals such as mice or rats and a case of using non-human animals wherein a gene function encoding Plexin-A1 is deficient or express excessively on chromosomes.

For example, to explain more concretely a screening method using a protein having an extracellular domain of Plexin-A1 and a target substance, the expressing cell under the existence of a target substance, detecting the decrease or increase of the amount of proteins having an extracellular domain of Plexin-A1 expressed on a surface of a cell membrane for a specific period after culturing, by immunochemistry or by using as an index the suppression or enhancement of mRNA. A method of detecting mRNA used here can be performed by DNA chip, northern hybridization and others, and other methods, and when using a cell transfected with a gene associated with a reporter protein such as luciferase at a downstream of Plexin-A1 promotor, it is possible to detect the suppression or enhancement of expressing Plexin-A1 gene by a target substance using an activity of the reporter gene as an index. Agents suppressing or enhancing Plexin-A1 expression selected by the screening can be used as a pharmacological composition used for treating a patient requiring the strengthening of Plexin-A1 expression, as a pharmacological composition used for treating a patient requiring the suppression of Plexin-A1 expression, for example, as a treating agent or a preventive agent for a patient having a disease caused by a disorder of Plexin-A1 expressing cells such as auditory nerves. More concretely, it can be an auditory disorder or an olfactory disorder.

EXAMPLES

In the following, the present invention will be explained more concretely using examples. The present invention, however, will not be restricted by the examples in any fashion.

Example 1

Production of a Monoclonal Antibody Specific to Plexin-A1 a cDNA fragment encoding amino acids (aa) 86 to 480 of a mouse Plexin-A1 protein is cloned by a normal method in pET-3c vectors (Biochem. Biophys. Res. Commun. 226, 524-529, 1996) to transfect it to a coliform. The expression and purification of a recombinant protein was performed by a reported method (J. Neurobiol. 29, 1-17, 1996). The lysate of recombinant proteins (5 ml/ml) was mixed with the same amount of Titer-Max (CytRx), and it was injected to a planter of rats (Wistar; Chubu Kagaku Shizai) anesthetized heavily with ether four times with each interval of two hours. On the third day after the last additional immunization, the lymphocytes obtained from inguinal and popliteal lymph nodes are fused with marrow cells (P3X63Ag8U1) by a previously described method (Dev. Biol. 122, 90-100, 1987). Hybridoma cells are cultured using Dulbecco's modified Eagle medium (DMEM; Nissui) containing 10% of Fetal Bovine Serum (FBS; JRH Bioscience) and 10% of hybridoma cloning factors (Igen). Screening of hybridoma clones are performed by an ELISA assay, followed by a reported method (Meth. Enzymol. 92, 168-174, 1983). The supernatant of a hybridoma culture positive to an ELISA assay is further treated for immunostaining of a tissue segment, and isolate Plexin-A1 specific hybridoma clone p1192.

A monoclonal antibody p1192 against a Plexin-A1 recombinant protein is used to examine the distributions of Plexin proteins in the nervous system. While this antibody bound to a cell expressing Plexin-A1 (see FIG. 4A), it did not bind to a cell expressing Plexin-A2 or a cell expressing Plexin-A3. In the immunoblotting of a mouse embryonic brain, it is found that the monoclonal antibody p1192 bound to a band of 180 kDa, which is considered to be a Plexin-A1 protein (see FIG. 5A). Further, while the binding patterns of the monoclonal antibody p1192 against a tissue segment correspond to the localization of mRNA of Plexin-A1 detected by in situ hybridization (ISH), it obviously differs from the localization of mRNA of Plexin-A2 or Plexin-A3. From the results mentioned above, it is shown that the monoclonal antibody p1192 specifically recognizes a Plexin-A1 protein.

Example 2

Immunostaining

An embryo or a brain at various developmental stages or after a birth of an ICR mouse (Chubu Kagaku Shizai) was settled overnight in 10 mM of phosphate-buffer saline buffer (PBS: pH7.4) containing 4% of paraformaldehyd. Following the reported methods (Dev. Biol. 170, 170, 207-222, 1995; J. Neurobiol. 29, 1-17, 1996), frozen segments (14 µm for the thickness) were prepared from an embryonic mouse brain or a brain of a mouse after birth, and were subjected to immunochemistry. First, after treating prepared frozen segments with anti-Plexin-A1 antibodies (p1192), anti-rat IgG antibodies (Amersham) fluorescence (cy-2 or cy-3) labeled to an anti-Plexin-A1 antibody were bound to the segments, and were observed under presence of the fluorescent microscope. Further, the day where a vaginal plug is detected will be called embryonic 0.5 day (E0.5) in the following.

Example 3

Immunoblotting

Cultured inferior colliculus cells (explained below) were solubilized in a buffer containing SDS, the proteins contained in this were separated buy electrophoresis by SDS-PAGE 12.5% of gel), and were transferred to nitrocellulose membranes (S&S). Nitrocellulose membranes (S&S) are incubated together with blocking reagent at 4° C. for 12 hours, followed by the incubation together with bound anti-Plexin-A1 antibodies p1192 for 2 hours. The bound anti-Plexin-A1 antibodies were visualized using anti-Plexin-A1 antibody and biotinylated anti-rat IgG (Amersham) and Elite Kit (Vector iaboratories).

Example 4

In Situ Hybridization

In situ hybridization was performed following the reported methods (J. Neurobiol. 29, 1-17, 1996). $^{35}$S-labeled antisense and sense cRNA probes are prepared by transcripting from subcloned cDNA fragments (Biochem. Biophys. Res. Commun. 226, 396-402, 1996; Biochem. Biophys. Res. Commun. 226, 524-529, 1996), corresponding to Plexin-A1/564 to 2732 bp of ORF, Plexin-A2/2233 to 2988 bp of ORF, and Plexin-A3/1296 to 2389 bp.

Example 5

Culture of Inferior Colliculus Tissues and Inferior Colliculus Isolated Cells

Inferior colliculus tissues were extracted from E16.5 mouse embryonic brains in a 30 mm of culture plat where collagen (Cellamatrix; Nitta Gelatin) applied using a DME medium containing 10% of FBS. The inferior colliculus cells were obtained by treating an inferior colliculus tissue using trypsin. The inferior colliculus cells were cultured at the cell density of 5×10$^5$ per a well of a 24 well plate where PLL (100 µg/ml) and mouse laminin (20 µg/ml; Gibco BRL). To obtain a culture that does not contain neurons, the first cell culture of the second day were separated to single cells with EDTA, and then cultured again afterwards.

Example 6

Transfection of Plexin-A1 cDNA

The cDNA encoding full-length mouse Plexin-A1 protein (aa1 to 1894; Biochem. Biophys. Res. Commun. 226, 524-529, 1996) was cloned by a ordinary method, Kozaks sequence (Nucleic Acid Res. 15, 8125-8148, 1987) was inserted before the first ATG, and the products were inserted to a cloning domain of an expressing vector pCAGGS (Gene 108, 193-199, 1991; provided by Dr. Miyazaki). The cDNA encoding mouse Plexin-A2 proteins (aa18 to 1884; Biochem. Biuophys. Res. Commun. 226. 396-402, 1996) and Prexin-A3 proteins (aa20 to 1872; Biochem. Biophys. Res. Commun. 226, 396-402, 1996), and signaling sequences (Neuron 14, 941-948, 1995) and myc-tag (GGEQKLISEEDL) (SEQ ID NO: 4) of mouse Sema3A were added to their N-terminals, and then inserted to an expressing vector pCAGGS. To obtain stable transformed cells expressing Plexin-A1 or Plexin-A2, a Plexin-A1 or Plexin-A2 expressing vector and pST-neoB (Mol. Cell. Biol. 7, 2745-2752, 1987) were inserted to L-cells by the calcium phosphate method (Mol. Cell. Biol. 7, 2745-2752, 1987) at the same time, and selected by G418 (GIBCO). To express temporarily Plexin-A2 or Plexin-A3 in a COS7 cell, Plexin-A2 or Plexin-A3 vectors were transfected using LipofectoAMINE reagent (GIBCO-BRL). The L cells and COS cells were cultured in a DME medium containing 10% of FBS.

Example 7

Production of Sema6C-Alkaline Phosphatase Fusion Proteins

A sequence of human placenta alkaline phosphatase (AP; Cell 63, 185-194, 1990) were fused to a C-terminal side of the cDNA (the portion corresponding to the 1st to 599th of encoding an extracellular domain of a short splicing variant of a rat Sema6C (Sema6C-S; Moll. Cell. Neurosci. 13, 9-23, 1999), His6-tag sequence (Current Protocols in Molecular Biology, vol. 2, 1996) was located at C-terminal, and then the product was inserted into a mammalian expressing vector pCEP4 (FEBS Lett. 333, 61-66, 1993, Invitrogen). The Sema6C-alkaline phosphatase fusion protein (Sema6C-S-AP) expressing vector were introduced into COS7 cell with a FUGENE6 transfection reagent (Roche), and the fusion protein Sema6C-S-AP was temporarily expressed in the culture supernatant. The culture supernatant was then collected, and Sema6C-S-AP was purified by affinity purification using Ni-NTA column (Qiagen) as previously reported (J. Neurosci. 17, 9163-9193, 1997).

Example 8

Cell Surface Connectivity of Sema6C-S-AP

Plexin-A1 expressing L cells and non-expressing cells (parent strain) was sprayed on a 24-well culture plate (Sumitomo Bakelite). The cells were subject to one-hour incubation on ice together with 250 μl of HBHA solution (Cell 63, 185-194, 1990) containing 1% of FCS and Sema6C-S-AP of various concentrations. After removing HBHA solution, the cells were lysed to 250 μl of lysis (10 mM of tris-HCl, 1% of tritonX-100; pH8.0). The AP activity of the cell lysis was measured by a colorimetric analysis as described previously (Cell 63, 185-194, 1990).

Example 9

Binding of Sema6C Against Cultured Neurons and Brains

After inferior colliculus tissue cultures or brains obtained from E16.5 mouse embryos were settled by methanol at 0° C. for 5 seconds, it is incubated with Sema6C-S-AP at 37° C. for one hour. These samples were washed by HBHA buffer 5 times, and the inferior colliculus tissue cultures were fixed again in PBS containing 4% of paraformaldehyde, and the brains were fixed again in PBS containing 50% of aceton and 2% of paraformaldehyde. The samples were washed by PBS, and the inherent AP was inactivated by one-hour incubation at 65° C. and they were washed by TBST, and then NBT/BCIP was added to visualize Sema6C-S-AP bound to the samples.

Example 10

Detection of Growth Cone Collapse

The dorsal root ganglions (DRG) obtained from E8 chicken embryos and E12.5 mouse embryos were cultured in PPL (100 μg/ml) and laminin (20 μg/ml; Gibco BRL), using a DMA medium containing 10% of FBS and 20 nG/ml of 2.5 S NGF (WAKO). The affinity-purified Sema6C-S-AP was added to the chicken DRGs at 20 hours in culture and to the mouse DRGs at 12 hours in culture. After one hour, the cultures were fixed with glutaraldehyde, and the numbers of nerve fibers with collapsed in growth cones were calculated under a microscopic view.

Example 11

Detection of Cell Morphological Change Induced by Sema6C

The L cells expressing Plexin-A1, the L cells expressing Plexin-A2, and the cells not expressing Plexin (parental L cell) were cultured for 2 days on a 24-well culture plate ($2 \times 10^4$ cells/well) with a 1:1 mixture of DMEM containing 10% of FBS and Ham-F12 (Nissui). 165 nM of Sema6C-S-AP was added to the cultures at 37° C. for one hour, and the cultures product were fixed to measure the size of the cells.

Example 12

Expression of Plexin in the Ventral Cochlear System

Example 12-1

Expression of Plexin in an Inner Ear

The expression of Plexin-A1 and Plexin-A3 in an inner ear was examined by in situ hybridization (ISH) and immunostaining. The result (micrograph) was shown in FIG. 1. FIG. 1A to FIG. 1D show the distributions of mRNAs of Plexin-A1 and Plexin-A3 detected by ISH analysis. FIG. 1A and FIG. 1B show the cases of hybridizing a tissue of an inner ear obtained from an E16.5 embryo with cRNA probe of Plexin-A1, and FIG. 1C and FIG. 1D show the cases of hybridizing a tissue of an inner ear with cRNA probe of Plexin-A3, respectively. While the ISH signaling of Plexin-A1 and Plexin-A3 cRNA probe is strong in the spiral ganglion (SG) and the vestibular ganglia (VG), it was weak in the cochlea receptors (CR), the utriculi macula (UM), the sacculi macula (SM), and the ampullaris crista (AC) a nonsensory epithelium of the membranous labyrinth (indicated by arrows).

FIG. 1E to FIG. 1H show the results of immunostaining of the segments of the inner ears obtained from E16.5 embryos by anti-Plexin-A1 antibody p1192. The monoclonal antibody p1192 bound to the spiral ganglia (SG) and their efferent fibers (VGe), and the afferent fibers (SGa), the vestibular ganglia (VG) and their efferent fibers (VGe), the cochlear receptors (CR), the ampullaris crista (AC), the sacculi macula (SM), and nonsensory epithelium in the membranous labyrinth (indicated by an arrow). A scale in FIG. 1A to FIG. 1D indicates 200 μm, and a scale in FIG. 1E to FIG. 1H indicates 100 μm, respectively.

As mentioned above, in E16.5 embryos, strong ISH signaling of mRNA of Plexin-A1 is detected in the spiral ganglia and the vestibular ganglia (FIGS. 1A, B), the immunostaining using a monoclonal antibody p1192 shows that Plexin-A1 proteins are localized in the spiral ganglion and its efferent and afferent fibers, the vestibular ganglia and their fibers (FIG. 1E to H), and while the ISH signaling of mRNA of Plexin-A1 was weak in the vestibular receptors such as the cochlea receptors (organ of corti; FIG. 1E), the ampullaris crista (FIG. 1F), the sacculi macula (FIG. 1H), and the utriculi macula, and a nonsensory epithelium in the membranous labyrinth (FIG. 1F). it was found that they were immuned positively to the monoclonal antibody p1192 (see FIGS. 1A and B). On the other hand, while the ISH signaling of mRNA of Plexin-A3 is strong in the spiral ganglion and the vestibular ganglia, but modulated in the membranous labyrinth of E16.5 embryos (FIGS. 1C, D). The mRNA transcripts of Plexin-A2 were not detected in the inner ear, and the spiral ganglia and the vestibular ganglion.

Example 12-2

Expression of Plexin in the Central Auditory Path

Figure 2:
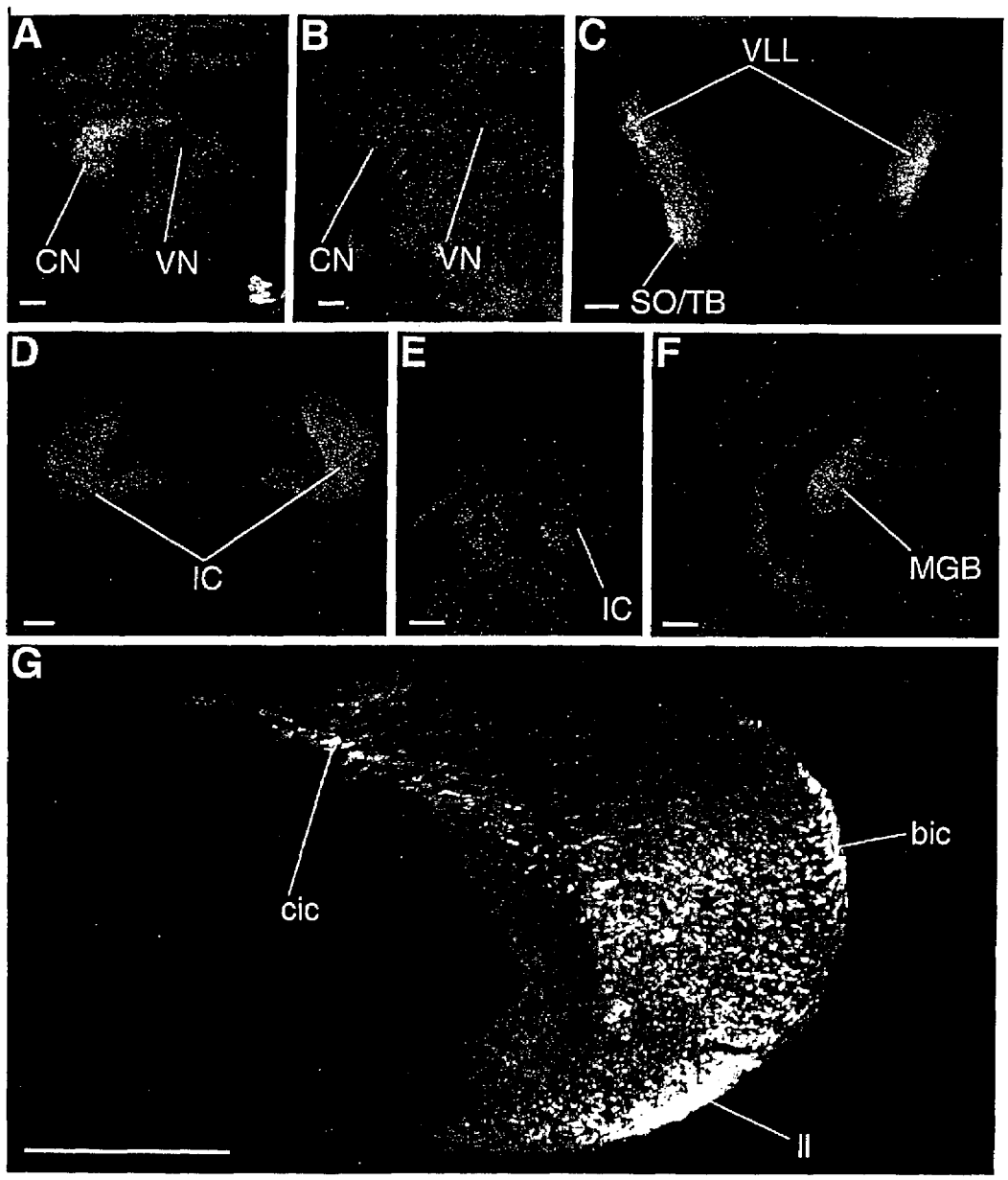
FIG. 2 shows the result of the expression of Plexin-A1, Plexin-A2 and Plexin-A3 in the central auditory pathway by in situ hybridization and immunostaining.

The expression of Plexin-A1, Plexin-A2 and Plexin-A3 in the central auditory path were examined by in situ hybridization (ISH) and immunostaining. The results (micrographs) were shown in FIG. 2. FIG. 2A, FIG. 2C, FIG. 2D and FIG. 2F show the distributions of mRNA of the Plexin-A1 in the brain stem detected by ISH analysis, FIG. 2E shows the distribution of mRNA of Plexin-A2, and FIG. 2B shows the distribution of mRNA of Plexin-A3. Strong ISH signaling with cRNA probe of Plexin-A1 was detected in the cochlear nucleus (CN), regions corresponding to the superior olive nucleus complex and the trapezoid body (So/TB), the ventral lateral lemniscus nucleus (VLL), the inferior colliculus (IC) and medial geniculate body (MGB). mRNA of Plexin-A2 was detected only in the central portion of the inferior colliculus, and the signaling of Plexin-A3 probe was detected in almost all parts of the brain stem. Further, FIG. 2G show the result of immunostaining of the inferior colliculus coronary segment by a monoclonal antibody p1192, and the antibody bound to the lateral lemniscus (ll), neuropil in the inferior collide (asterisk), the brachium of the inferior colliculus (bic) and the commissural fibers of the inferior colliculus (cic). A scale in FIG. 2 indicates 200 μm, and a scale in FIG. 1E to FIG. 1H indicates 100 m, respectively.

As shown above, the expression of Plexin-A1 is recognized in all the nuclei constituting the central auditory path, and while the ISH signaling with CRNA probe of an E16.5 embryo was detected in dorsal and ventral cochlea nuclei that receive pars cochlearis (FIG. 2A), a region corresponding to an superior olive nucleus complex and a trapezoid body, and ventral and dorsal ciliary body nuclei (FIG. 2C), it was very weak or almost undetectable in ventral nucleus (VN) that receives a ventral nerves (See FIG. 2A). The expression of Plexin-A1 was most remarkable in an inferior colliculus where all the ascending fibers out of an auditory brain stem (lateral lemniscus) converges, or medial lemniscus pulvinar (brachium colliculi inferioris) that receives a fiber from an inferior colliculus (FIG. 2F), almost all the portions of neopallium including an auditory epithelium was expressed (data not shown). Further, a strong immunopositive reaction was recognized in a lateral lemniscus, brachium colliculi inferioris and commissural neurofibers of a inferior collide (FIG. 2G). Further, while Plexin-A1 was expressed in all the central nuclei from the mouse auditory paths of 0 day (P0) and 3 day (P3) after birth, it was not expressed in matured mice (data not shown).

On the other hand, Plexin-A2 was not expressed in an auditory and ventral pathway except for the central portion of an inferior colliculus (FIG. 2E), and the ISH signaling against the mRNA from Plexin-A3 were detected in most portions of CNS (central nervous system) comprising a central nuclear of E16.5 embryos (FIG. 2B) and P0 and P3 mouse auditory and a ventral pathway, it was not detected in adult mice.

Example 13

Expression of Plexin in the Olfactory System

Figure 3:
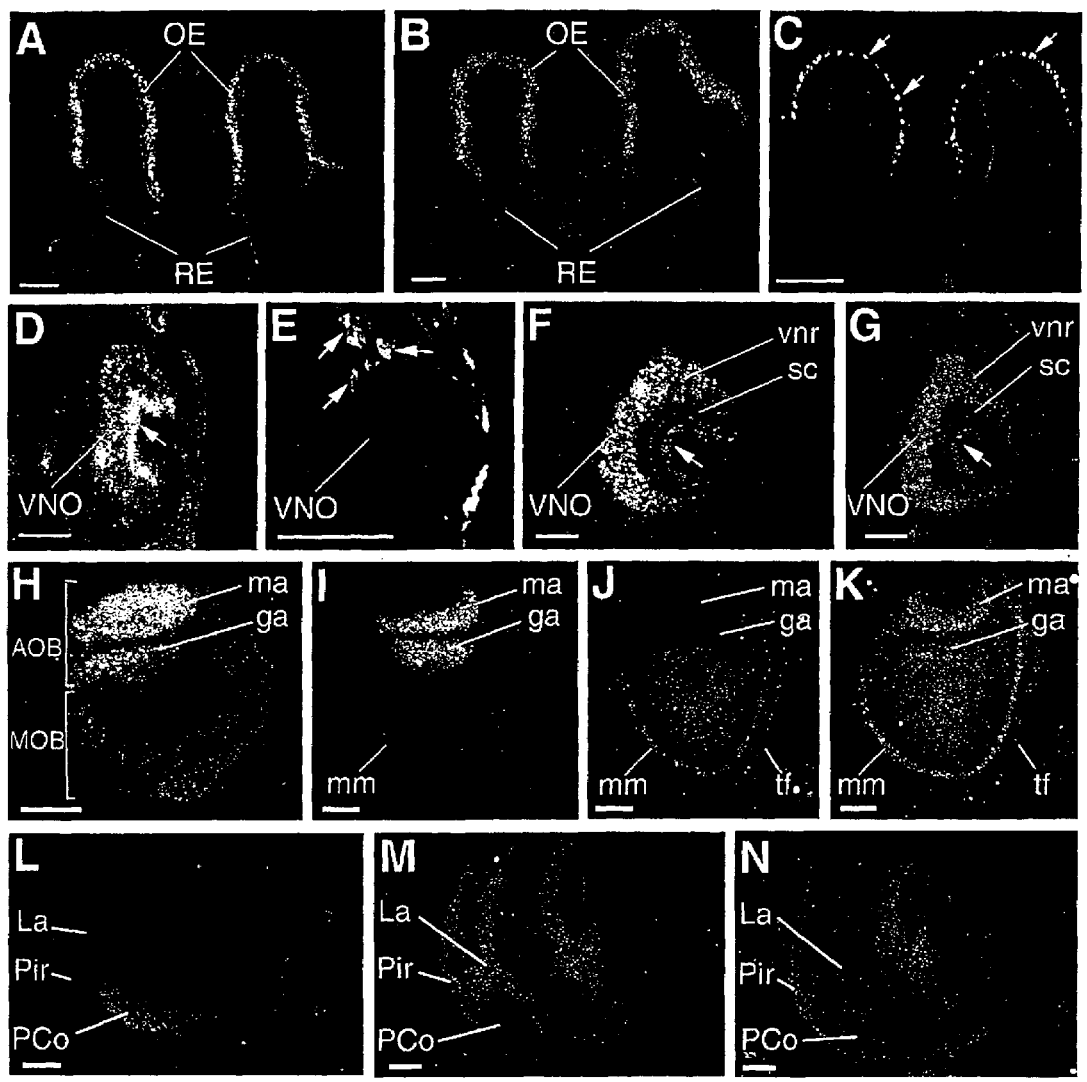
FIG. 3 shows the result of the expression of Plexin-A1, Plexin-A2 and Plexin-A3 in the olfactory pathway by in situ hybridization and immunostaining.

The olfactory system of vertebrates can be divided to two neuronal paths that are anatomically and functionally different. The expression of Plexin-A1, Plexin-A2 and Plexin-A3 in the olfactory system are examined by in situ hybridization (ISH) and immunostaining. FIG. 3 shows the result (micrograph), and it is found that the three mouse Plexins show different patterns of expression in the two olfactory paths. A scale in FIG. 3 indicates 200 μm.

Example 13-1

FIG. 3A and FIG. 3B show the distribution of mRNA of Plexin-A1 and the distribution of mRNA of Plexin-A3 in segments of nasal cavity coronal of E16.5 embryos, respectively. Strong signaling against both Plexin-A1 probe and Plexin-A3 probe was detected on olfactory epithelium (OE), and the middle level of signaling was detected on an aspiration epithelium. Further, FIG. 3C shows the result of immunostaining of a segment of nasal cavity of E16.5 embryos by a monoclonal antibody p1192, and it was observed that the antibody was bound to an olfactory neural fiber (indicated by an arrow). Further, FIG. 3D and FIG. 3F show the distributions of mRNA of Plexin-A1 in segments of E16.5 embryos and P0 mouse vomeronasal organ (VNO). While the ISH signaling against Plexin-A1 probe and Plexin-A3 probe was detected in a vomeronasal receptor layer (vnr) and a nonsensory epithelium (indicated by an arrow in FIG. 3F and FIG. 3G), it was not detected in supportive cell layer (sc). Further, FIG. 3E shows the result of immunostaining of the segments of a vomeronasal organ of E16.5 embryos and indicates that Plexin-A1 proteins are localized in a vomeronasal nerves (indicated by an arrow).

As noted above, the ISH signaling against mRNA of Plexin-A1 is detected on sensory epithelium of both nasal cavity (FIG. 3A9 and vomeronasal organ (FIG. 3D) of E16.5 embryos, the expression of Plexin-A1 on a vomeronasal sensory epithelium is stronger in P0 mouse (FIG. 3F), and the detection is limited to sensory cell layer rather than supportive cell layer. Further, it was found that Plexin-A1 proteins were localized in olfactory cell fibers (FIG. 3C) and a vomeronasal nervous fiber (FIG. 3E) by immunohistochemistry using an monoclonal antibody p1192. On the other hand, while the ISH signaling of Plexin-A3 against mRNA was found on an E16.5 embryos and olfactory epithelium and vomeronasal epithelium from P0 and P3 mice (FIG. 3B and FIG. 3G), it was restricted to the sensory cell layer in vomeronasal epithelium. Further, while the expression of mRNA by Plexin-A1 and Plexin-A3 does not show any regional difference within the area of vomeronasal sensory epithelium, mRNA of Plexin-A2 was not expressed on olfactory epithelium and vomeronasal epithelium at any examined stage of the development.

Example 13-2

Expression of Plexin in an Olfactory Bulb

FIG. 3H and FIG. 3I show the distributions of mRNA of Plexin-A1 from E16.5 embryos and P3 mouse coronary segments of olfactory bulbs, respectively, and FIG. 3J and FIG. 3K show the distributions of mRNA of Plexin-A2 and Plexin-A3 in the coronary segments of olfactory bulbs from P3 mouse. While Plexin-A1 was strongly expressed in mitral cells layer (ma) and granule cell layer (gm) of E16.5 embryos, it was strongly expressed in mitral cells layer (ma) and granule cell layer (gm) of the main olfactory bulb (MOB) (FIG. 3H). Stria olfactoria lateralis constituted from an afferent fiber from the main olfactory bulb and accessory olfactory bulb was positive to the monoclonal antibody p1192 (data not shown). In P0 and P3 mice, while the expression of Plexin-A1 is remarkably decreasing in the main olfactory bulb, it was weak in an accessory olfactory bulb (FIG. 3I). Further, Plexin-A1 mRNA was not detected in a matured olfactory bulb. On the other hand, the expression of Plexin-A2 in an olfactory bulb is almost complementary against the Plexin-A1, the ISH signaling against mRNA of Plexin-A2 was observed in a mitral cell layer (mm) and a tufted filiation cell layer (tf) of the main olfactory bulb (MOB) of E16.5 embryos and P0 and P3 mice, but it was not observed in accessory olfactory bulb (FIG. 3J). Further, the expression of Plexin-A2 in a main olfactory bulb of a matured mouse was weak. On the other hand, Plexin-A3 was expressed in a mitral cell and a granule cell of a main olfactory bulb and in a mitral cell and a granule cell of an accessory olfactory bulb of E 16.5 embryo and P0 and P3 mice (FIG. 3K), they were expressed weakly in mitral cells both a the main olfactory bulb and an accessory olfactory bulb.

Example 13-3

Expression of Plexin in the Olfactory Path

FIG. 3L to FIG. 3N show the distributions of mRNA of Plexin-A1, mRNA of Plexin-A2, and mRNA of Plexin-A3 in coronary segments prepared from a caudal telencephalon of E16.5 embryo, and it was found that the three Plexin shows different patterns of expression in the central nucleus of an olfactory path. That is, the strong signaling of Plexin-A1 against mRNA was detected in the central nucleus of an accessory olfactory bulb, such as a posterior cortex amygdaloidal nucleus (Pco) and a ventral amygdaloidal nucleus, but it was not detected in the nucleus of a main olfactory pathway (FIG. 3L). On the other hand, the ISH signal against Plexin-A2 was detected in the central nucleus of the main olfactory path such as a ventral olfactory, a piriform cortex (Pir), an olfactory infield cortex and a lateral amnygdaloidal nucleus (La), and it was not detected in the nucleus of an accessory olfactory bulb (FIG. 3M). Plexin-A3 was detected in all the central olfactory nuclei in both of the main olfactory path and a subolfactory pathway (FIG. 3N). Further, the three expression patterns of Plexin in the central olfactory nucleus were the same as the ones in the 16.5 embryos. While the ISH signaling of Plexin-A2 and Plexin-A3 against mRNA was detected in the central nucleus of main olfactory path, the ISH signaling of mRNA of Plexin-A1 was not detected.

Example 14

Identification of Sema6C as a Ligand for Plexin-A1

Figure 4:
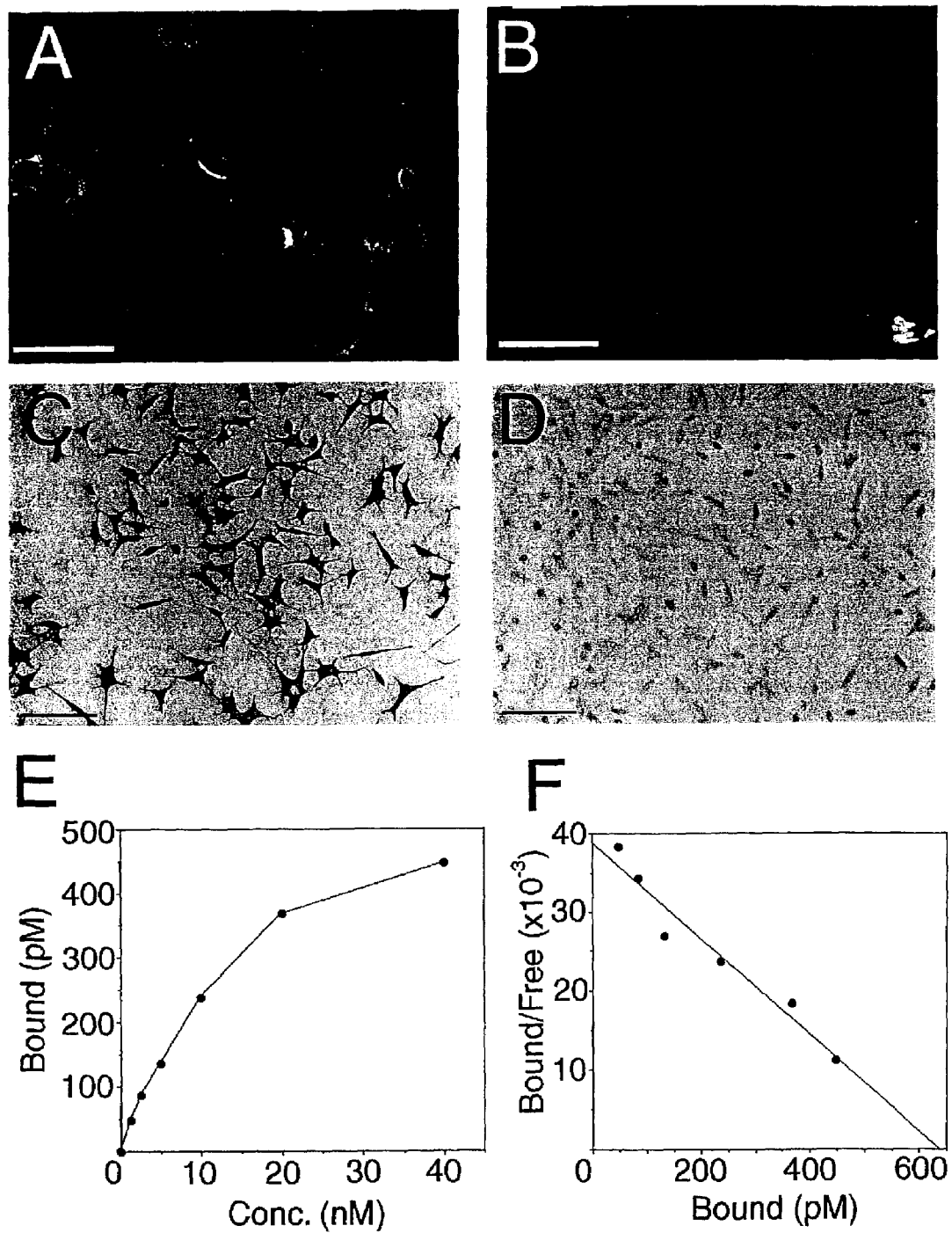
FIG. 4 comprises the figures showing the binding of Sema6C-AP against L cells expressing Plexin-A1 (A to D), and the graphs (E, F).

In order to gain further insights on the function of a ligand in the development of the nervous system, it is essential to identify the identification of a ligand that interacts with Plexin, and to screen such a ligand, a transfectant expressing Plexin-A1 was obtained by transfecting a L cell with cDNA of a full-length mouse Plexin-A1, following the method described in Example 6. FIG. 4A and FIG. 4B show the results of immunohistochemistry of a L cell expressing Plexin-A1 using an anti-Plexin-A1 antibody p1192, and a L cell not expressing Plexin-A1 as a control. Since the antibody is bound only to the surface of a L cell expressing Plexin-A1, it was confirmed that Plexin-A1 was localized on the surface of a cell of a transfectant.

Next, secretory and transmembrane semaphorins bound to a transfectant expressing Plexin-A1 were screened, and it was confirmed that Sema6C bound to Plexin-A1 in the following way. First, to carry out an experiment of binding Plexin-A1, a recombinant protein (Sema6C-S-AP) was prepared with an AP-tag at the extracellular domain of an isoform (Sema6C-S) lacking a region of 32 amino acids among two splicing isoforms with or without 32 amino acids of an extracellular domain of Sema6C. The Sema6C-S-AP and the transfectants (an L cell expressing Plexin-A1) were used to perform a binding experiment. FIG. 4C shows that Sema6C-S-AP strongly bound to a cell not expressing Plexin-A1 (parent cell), and FIG. 4D shows that it does not strongly bind to a L cell not expressing Plexin-A1 (parent strain) as a contrast. A scale in FIG. 4A to D indicates 100 μm.

Further, following the method described in Example 8, a quantitative analysis regarding the binding of Sema6C-S-AP against Plexin-A1 were carried out. FIG. 4E shows the result. In FIG. 4E, the AP activity caused by the non-specific binding with a Plexin-A1 non-expressing L cell was subtracted to obtain the specific binding of Sema6C-S-AP against Plexin-A1. Further, Scatchard Plot derived from the data in FIG. 4E was shown in FIG. 4F, and presumptive dissociation constant ($K_D$) of binding of Plexin-A1 with Sema6C-S-AP was 16.5 nM. Further, the binding of Sema6C-S-AP with Plexin-A1 was not blocked neither by the monoclonal antibody p1192 nor the antiserum against Plexin-A1 recombinant protein. Further, Sema6C-S-AP did not bind to a PCOS 7 cell expressing Plexin-A2 or Plexin-A3, and it did not bind to an L cell expressing neuropilin-1. An extracellular domain such as AP fusion Sema3A (Cell 90, 753-762, 1997), AP fusion Sema4C (M-Sema F; FEBS lett. 370, 269-272, 1995) or AP fusion Sema4D (M-Sema G; J/Biol. Chem. 271, 33376-33381, 1996) or a fusion protein of immunoglobulin Fc region and AP were not bound to a cell expressing Plexin-A1.

Example 15

Binding of Sema6C Against Neurons

Figure 5:
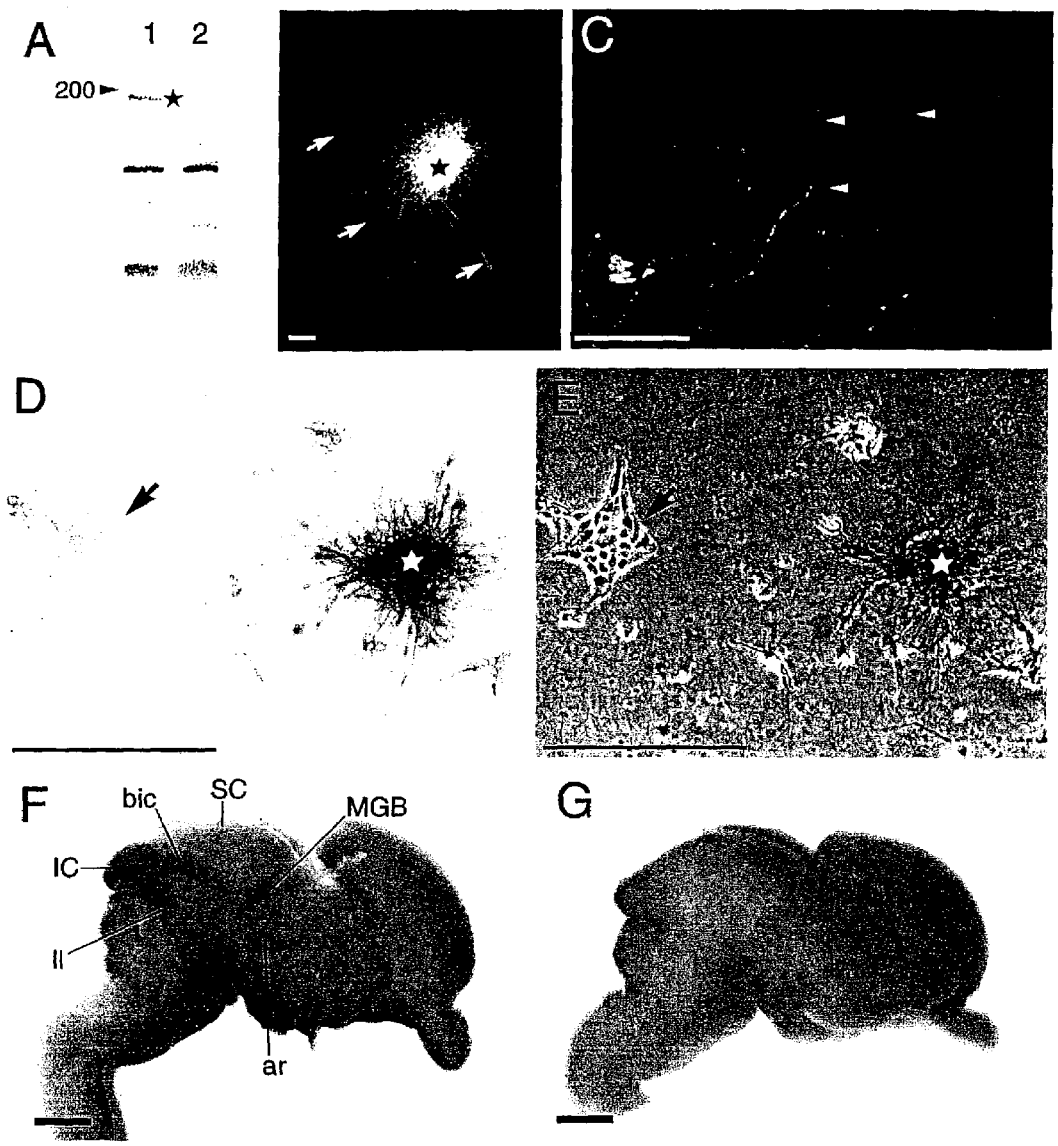
FIG. 5 shows an immunoblotting electroporation of Plexin-A1 in the expressing L cells (A), and the binding of Sema6C to the cultured inferior colliculus neurons and the auditory pathway.

To confirm that Sema6C is bound to a natural Plexin-A1 protein expressed in a neuron, E16 mouse embryonic inferior colliculus isolated cell was prepared following the method described in Example 5. The primary cultured cells obtained by two-day culture contained a number of neurons. Further, the second culture was carried out from the first culture to prepare the ones that do not contain neurons but contain a number of glial cells. When immunoblotting was performed for the cells using a monoclonal antibody p1192, p1192 positive bands considered to be Plexin-A1 protein at 180 kDa was detected in the lysis of an inferior primary culture containing a number of neurons (the asterisk in lane 1 of FIG. 5A) while it was not detected in the second culture that does not contain neurons but contains glial cells (FIG. 5A lane 2). These results show that Plexin-A1 is expressed in a neuron but not in a glial cell. Further, immunostaining against an inferior colliculus explant culture of E16.5 embryo by a monoclonal antibody p1192 revealed that an inferior colliculus fragment (the asterisk in FIG. 5B), axons (the arrow in FIG. 5B) and growth cone (the arrowhead in Fig. C) is immunopositive against a monoclonal antibody p1192, and it was shown that most of the inferior colliculus neurons express Plexin-A1.

Next, FIG. 5D (bright-field image) and FIG. 5E (phase-contrast image) show the results of examination of the binding of Sema6C-S-AP to the inferior colliculus segments. These results show that while Sema6C-S-AP is bound to an explant containing neurons (asterisk) and an axon, it does not bind to a non-neural cell (arrowhead). Sema6C-S-AP was not bound to a cultured anterior colliculus neurons that do not express Plexin-A1 (see FIG. 2D). Further, FIG. 5F and FIG. 5G show the results of binding of Sema6C-S-AP and AP (10 nM) against an dissected E16.5 embryonic brain. A remarkable amount of Sema6C-S-AP was detected at the regions where a large amount of Plexin-A1 proteins in an dissected brain obtained from an E16.5 embryo, that is, an auditory nervous nucleus and fascicles containing acoustic radiation out of a lateral lemniscus (ll), inferior colliculus (IC), brachium of the inferior colliculus (bic), medial geniculate body (MGB). A scale in FIG. 5B is 100 μm, FIG. 5C is 50 μm, FIG. 5D and FIG. 5E are 250 μm, and FIG. 5F and FIG. 5G is 1 mm.

Example 16

Growth Cone Collapse Induced by Sema6C

Figure 6:
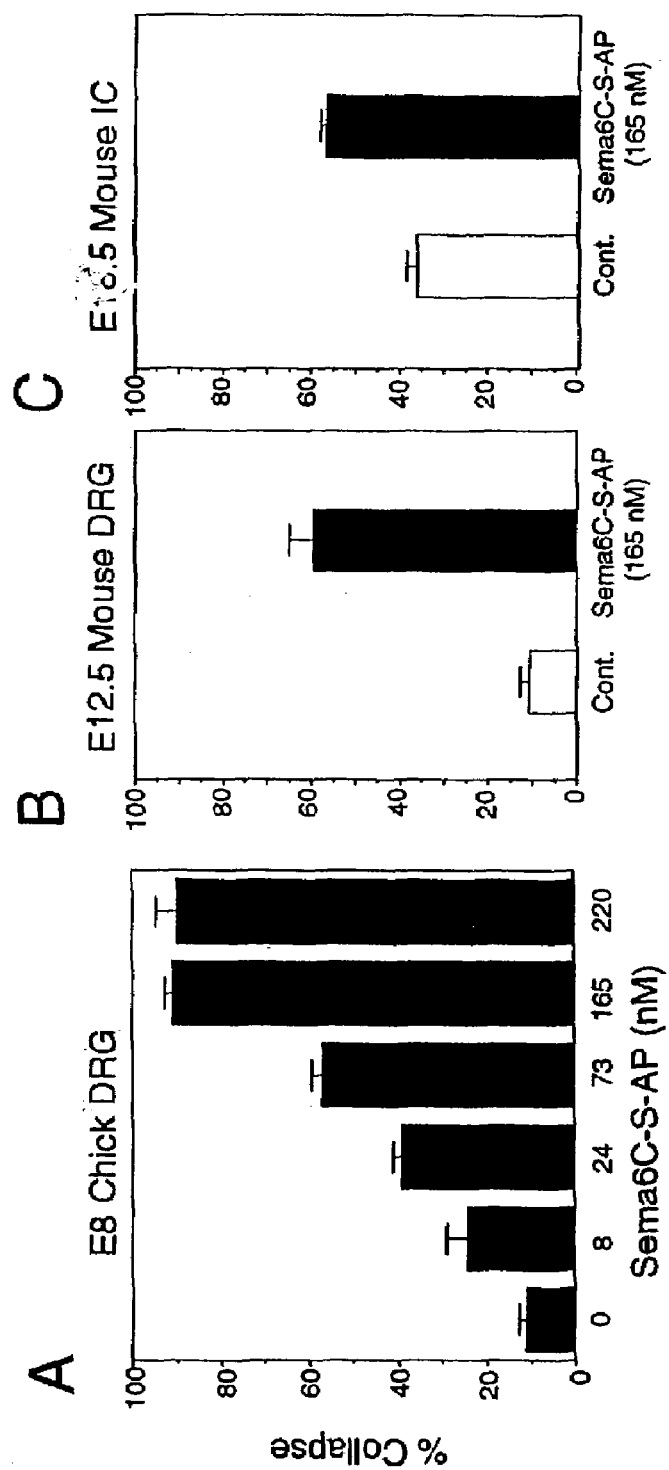
FIG. 6 comprises graphs showing the growth cone collapse activity of Sema6C.

Affinity-purified Sema6C-S-AP was added to an explant culture of dorsal root ganaglion (DRG) neurons obtained from an E8 chicken embryo and an E12.5 mouse embryo and obtained form an E16.5 mouse embryo, and was treated at 37° C. for an hour, and the growth cone collapse activity of Sema6C was measured following the description in Example 10. FIG. 6A to FIG. 6C show each of the results. As shown in FIG. 6A (an average percent of the growth cone collapse obtained by three independent tests), Sema6C-S-AP causes the collapse of growth cone in a dose-dependent fashion on a chicken embryonic DRG, almost 100% of the growth cone collapse was observed by adding 165 nM. In contrast, as shown in FIG. 6B and FIG. 5C (average percent obtained from three independent tests from each other), when the same amount (165 nM) of Sema6C (black column) or a contrastive buffer (Cont; empty column; 10 mM of HEPES containing 1% of FBS; a dialytic buffer against Sema6C-S-AP recombinant protein) was added to the culture (FIG. 6B; p=0.001), Sema6C-S-AP induced 50% of the growth cone collapse bind a mouse embryonic DRG neuron (FIG. 6B; p=0.001), and 20% of the growth cone collapse was observed in Sema6C-S-AP against a cultured inferior colliculus neuron (FIG. 6C; p=0.001).

Example 17

Cell Shrinkage Induced by Sema6C

Figure 7:
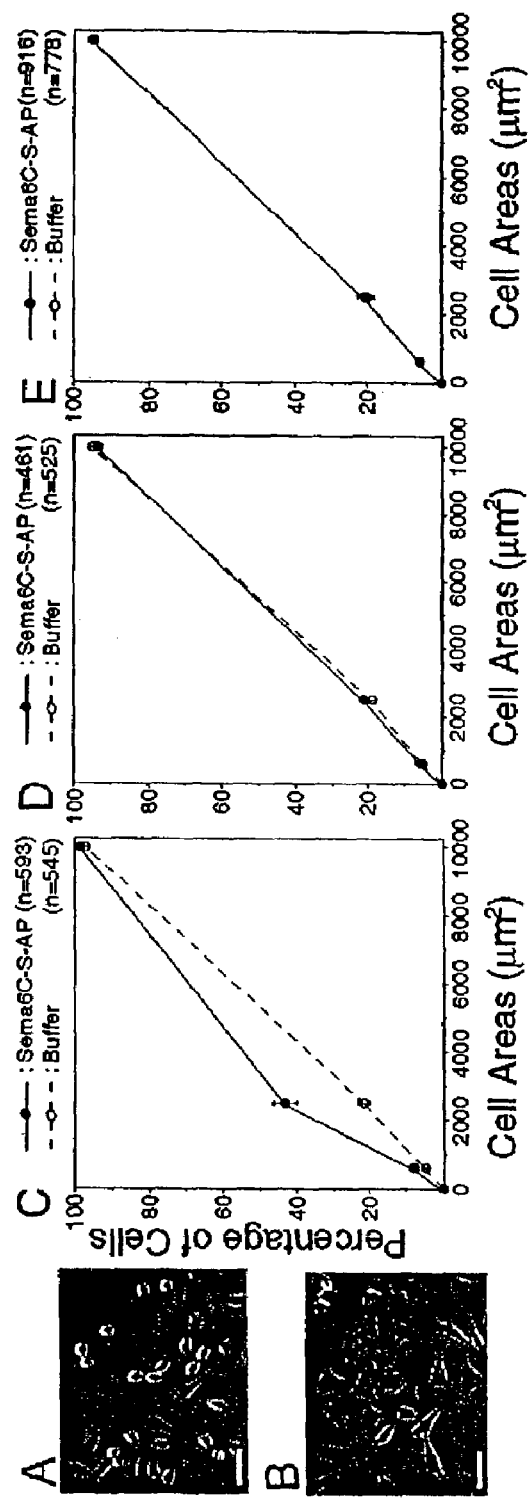
FIG. 7 comprises the figures showing morphological changes in cells induced by Sema6C (A, B), and the graphs (C to E).

To examine whether Plexin-A1 can transmit a signaling induced by Sema6C into a cell, morphology of a cell was observed following the method described in Example 11, by adding Sema6C-S-AP to a cell expressing Plexin-A1, a cell expressing Plexin-A2 and an L cell not expressing Plexin. FIG. 7 shows the morphological change of each cell after one-hour culture at 37° C. by adding 165 nM of Sema6C-S-AP or a contrastive buffer (a dialytic buffer for Sema6C-S-AP) to a cell expressing Plexin-A1, a cell expressing Plexin-A2 and a cell not expressing Plexin. FIG. 7A and FIG. 7B show the result (Phase-Contrast Microscope) of cells expressing Plexin-A1 treated by Sema6C-S-AP or treated by a contrastive buffer, and FIG. 7C to FIG. 7E show that the result of the quantitative analysis regarding the cell size of a cell expressing Plexin-A1, a cell expressing Plexin-A2 and a cell not expressing Plexin that were treated by Sema6C-S-AP or by a contrastive buffer was shown by plotting a cell percent of a square smaller than 25×25 µm$^2$ (625 to m$^2$), 50×50 µm$^2$ (2,500 µm$^2$) and 100×100 µm$^2$ (10,000 µm$^2$). Each point indicated in FIG. 7C to FIG. 7E is an average percent of 9 independent regions obtained by 3 wells. A scale in FIG. 7A and FIG. 7B represents 50 µm.

165 nM of Sema6C-S-AP enough to induce a complete collapse of the growth cone of chicken DRG neurons (see FIG. 6A) was added to a cell expressing Plexin-A1, and fixed at 37° C. for an hour. The measurement of the cell size revealed that they remarkably shrank (FIG. 7A). Further, semi-quantitative measurement of the cell size showed that the size of a cell expressing Plexin-A1 remarkably shrank by Sema6C-S-AP (FIG. 7C). Even a cell expressing Plexin-A2 (FIG. 7D) or a cell not expressing Plexin (FIG. 7E) was treated by the same amount (165 nM) of Sema6C-S-AP, no morphological change was recognized. From the results that while Sema6C-S-AP induced a shrinkage of the size of an L cell expressing Plexin-A1, it did not induce a shrinkage of an L cell expressing Plexin-A2 or an L cell not expressing Plexin, it was confirmed that a signaling induced by Sema6C was transmitted into a cell by the specific interaction of Sema6C against Plexin-A1.

Example 18

Screening of an Antagonist of Sema6C Using a Cell Expressing Plexin-A1

An antagonist of Sema6C can be screened by adding further target substances to the binding experiments of Sema6C-S-AP to a cell expressing Plexin-A1, described in Example 14. That is, the use of Sema6C-S-AP prepared by the method described in Example 7 and the transformant expressing a Plexin-A1 protein prepared by the method described in Example 6 on the surface of the cell, and the connectivity of the Sema6C-S-AP to the expressing cell was detected by the alkaline phosphatase activity, and select a target substance wherein the AP activity is lower in (ii) than (I), or there is no AP activity in cases of (i) when Sema6C-S-AP was added, and (ii) Sema-S-AP and a target substance were added, against the cell expressing Plexin-A1.

INDUSTRIAL APPLICABILITY

The present invention provides a screening method for an agonist or an antagonist of Sema6C using Plexin-A1, or a screening tool for the screening tool. Further, since Sema6C has a growth cone collapse activity against a nervous cell and a contractile activity against a cell, an agonist or antagonist of Sema6C obtained by a screening method of the present invention is useful as agents for treating or preventing the diseases caused by the lack or excessive expression of Sema6C

What is claimed:

1. A screening method for agonists or antagonists of Semaphorin 6C, comprising the steps of:
   a) measuring in an in vitro assay system the binding activity of a protein with an extracellular domain of Plexin-A1, comprising the 1$^{st}$ to 1237$^{th}$ amino acid residues in the sequence of Plexin-A1, consisting of SEQ ID NO:5 or SEQ ID NO:6, to a protein having an extracellular domain of Semaphorin 6C, comprising the 1$^{st}$ to 599$^{th}$ amino acid residues in the sequence of Semaphorin 6C, consisting of SEQ ID NO:7, SEQ ID NO:8, SEQ ID NO:9 or SEQ ID NO:10, in the presence and absence of a target substance, and
   b) selecting the target substance as a candidate for an agonist or antagonist of Semaphorin 6C if there is a decrease in said binding activity in the presence of said target substance compared to an assay in which the target substance is absent.

2. The screening method of claim 1 wherein the Semaphorin 6C is a human, mouse or rat Semaphorin 6C.

3. The screening method for agonists or antagonists of Semaphorin 6C according to claim 1.

4. The screening method for agonists or antagonists for Semaphorin 6C according to claim 1, wherein the protein having the extracellular domain of Semaphorin 6C is a protein bound to a marker protein and/or a peptide tag.

5. The screening method for agonists or antagonists for Semaphorin 6C according to claim 4, wherein the marker protein is alkaline phosphatase or an immunoglobulin Fc domain.

6. The screening method for agonists or antagonists for Semaphorin 6C according to claim 1, wherein a cell membrane or a cell expressing a protein with the extracellular domain of Plexin-A1 is used.

7. The screening method for agonists or antagonists for Semaphorin 6C according to claim 6, wherein the cell membrane or cell expressing protein having the extracellular domain of Plexin-A1 is, or is obtained from, a stable transformant.

8. The screening method for agonists or antagonists for Semaphorin 6C according to claim 1, wherein the protein having the extracellular domain of Plexin-A1 is a recombinant protein.

9. The screening method for agonists or antagonists for Semaphorin 6C according to claim 1, wherein the protein having the extracellular domain of Plexin-A1 is Plexin-A1.

10. A screening method for agonists or antagonists of Semaphorin 6C, comprising the steps of
    1) contacting Plexin-A1 consisting of SEQ ID NO:5 or SEQ D NO:6 with a target substance in an in vitro assay system, and
    2) measuring Semaphorin 6C activity in said assay system by detecting the presence or absence of a signal arising from an interaction between a protein having an extracellular domain of Semaphorin 6C comprising the 1$^{st}$ to 599$^{th}$ amino acid residue in the sequence of Semaphorin 6C consisting of SEQ ID NO:7, SEQ ID NO:8, SEQ ID NO:9 or SEQ ID NO:10 and Plexin-A1, wherein the signal is
       i) a growth cone collapse activity, or
       ii) a contractile activity of a Plexin-A1 expressing cell,
    wherein a decrease in said Semaphorin 6C activity indicates that said target substance is an antagonist and an increase in said Semaphorin 6C activity indicates that said target substance is an agonist.

11. The screening method of claim 10 wherein the Semaphorin 6C is a human, mouse or rat Semaphorin C.

12. The screening method for agonists or antagonists of Semaphorin 6C according to claim 10, wherein the protein is recombinant.

* * * * *

```
SEQUENCE LISTING

<160> NUMBER OF SEQ ID NOS: 10

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence:
      Illustrative Myc tag sequence

<400> SEQUENCE: 1

Glu Gln Lys Leu Ile Ser Glu Glu Asp Ile
1               5                   10

<210> SEQ ID NO 2
<211> LENGTH: 6
<212> TYPE: PRT
<213> ORGANISM: Artificial Sequence
<220> FEATURE:
```

```
<223> OTHER INFORMATION: Description of Artificial Sequence:
      Illustrative 6X His tag sequence

<400> SEQUENCE: 2

His His His His His His
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence:
      Illustrative Flag tag sequence

<400> SEQUENCE: 3

Asp Tyr Lys Asp Asp Asp Asp
1               5

<210> SEQ ID NO 4
<211> LENGTH: 12
<212> TYPE: PRT
<213> ORGANISM: Murine sp.

<400> SEQUENCE: 4

Gly Gly Glu Gln Lys Leu Ile Ser Glu Glu Asp Leu
1               5                   10

<210> SEQ ID NO 5
<211> LENGTH: 1754
<212> TYPE: PRT
<213> ORGANISM: Homo sapiens
<220> FEATURE:
<221> NAME/KEY: misc_feature
<222> LOCATION: (78)..(78)
<223> OTHER INFORMATION: The 'Xaa' at location 78 stands for Asn, Ser,
      Thr, or Ile.
<220> FEATURE:
<221> NAME/KEY: misc_feature
<222> LOCATION: (123)..(123)
<223> OTHER INFORMATION: The 'Xaa' at location 123 stands for Asn, Asp,
      His, or Tyr.
<220> FEATURE:
<221> NAME/KEY: misc_feature
<222> LOCATION: (620)..(620)
<223> OTHER INFORMATION: The 'Xaa' at location 620 stands for Ile, Val,
      or Leu.
<220> FEATURE:
<221> NAME/KEY: misc_feature
<222> LOCATION: (1474)..(1474)
<223> OTHER INFORMATION: The 'Xaa' at location 1474 stands for Gln, Arg,
      Pro, or Leu.

<400> SEQUENCE: 5

Gly Met Trp Ala Glu Ala Gly Leu Pro Arg Ala Gly Gly Gly Ser Gln
1               5                   10                  15

Pro Pro Phe Arg Thr Phe Ser Gly Ser Asp Trp Gly Leu Thr His Leu
            20                  25                  30

Leu Val His Glu Gln Thr Gly Glu Val Tyr Val Gly Ala Val Asn Arg
        35                  40                  45

Ile Tyr Lys Leu Ser Gly Asn Leu Thr Leu Leu Arg Ala His Val Thr
    50                  55                  60

Gly Pro Val Glu Asp Asn Glu Lys Cys Tyr Pro Pro Xaa Val Gln
65                  70                  75                  80

Ser Cys Pro His Gly Leu Gly Asn Thr Asp Asn Val Asn Lys Leu Leu
                85                  90                  95
```

-continued

```
Leu Leu Asp Tyr Ala Ala Asn Arg Leu Leu Ala Cys Gly Ser Ala Ser
            100                 105                 110

Gln Gly Ile Cys Gln Ser Leu Arg Leu Asp Xaa Leu Phe Lys Leu Gly
        115                 120                 125

Glu Pro His His Arg Lys Glu His Tyr Leu Ser Ser Val Gln Glu Ala
    130                 135                 140

Gly Ser Met Ala Gly Val Leu Ile Ala Gly Pro Gly Gln Gly Gln
145                 150                 155                 160

Ala Lys Leu Phe Val Gly Thr Pro Ile Asp Gly Lys Ser Glu Tyr Phe
                165                 170                 175

Pro Thr Leu Ser Ser Arg Arg Leu Met Ala Asn Glu Glu Asp Ala Asp
            180                 185                 190

Met Phe Gly Phe Val Tyr Gln Asp Glu Phe Val Ser Ser Gln Leu Lys
        195                 200                 205

Ile Pro Ser Asp Thr Leu Ser Lys Phe Pro Ala Phe Asp Ile Tyr Tyr
    210                 215                 220

Val Tyr Ser Phe Arg Ser Glu Gln Phe Val Tyr Tyr Leu Thr Leu Gln
225                 230                 235                 240

Leu Asp Thr Gln Leu Thr Ser Pro Asp Ala Ala Gly Glu His Phe Phe
                245                 250                 255

Thr Ser Lys Ile Val Arg Leu Cys Val Asp Asp Pro Lys Phe Tyr Ser
            260                 265                 270

Tyr Val Glu Phe Pro Ile Gly Cys Glu Gln Ala Gly Val Glu Tyr Arg
        275                 280                 285

Leu Val Gln Asp Ala Tyr Leu Ser Arg Pro Gly Arg Ala Leu Ala His
    290                 295                 300

Gln Leu Gly Leu Ala Glu Asp Glu Asp Val Leu Phe Thr Val Phe Ala
305                 310                 315                 320

Gln Gly Gln Lys Asn Arg Val Lys Pro Pro Lys Glu Ser Ala Leu Cys
                325                 330                 335

Leu Phe Thr Leu Arg Ala Ile Lys Glu Lys Ile Lys Glu Arg Ile Gln
            340                 345                 350

Ser Cys Tyr Arg Gly Glu Gly Lys Leu Ser Leu Pro Trp Leu Leu Asn
        355                 360                 365

Lys Glu Leu Gly Cys Ile Asn Ser Pro Leu Gln Ile Asp Asp Asp Phe
    370                 375                 380

Arg Gly Gln Asp Phe Asn Gln Pro Leu Gly Gly Thr Val Thr Ile Glu
385                 390                 395                 400

Gly Thr Pro Leu Phe Val Asp Lys Asp Asp Gly Leu Thr Ala Val Ala
                405                 410                 415

Ala Tyr Asp Tyr Arg Gly Arg Thr Val Val Phe Ala Gly Thr Arg Ser
            420                 425                 430

Gly Arg Ile Arg Lys Ile Leu Val Asp Leu Ser Asn Pro Gly Gly Arg
        435                 440                 445

Pro Ala Leu Ala Tyr Glu Ser Val Val Ala Gln Glu Gly Ser Pro Ile
    450                 455                 460

Leu Arg Asp Leu Val Leu Ser Pro Asn His Gln Tyr Leu Tyr Ala Met
465                 470                 475                 480

Thr Glu Lys Gln Val Thr Arg Val Pro Val Glu Ser Cys Val Gln Tyr
                485                 490                 495

Thr Ser Cys Glu Leu Cys Leu Gly Ser Arg Asp Pro His Cys Gly Trp
            500                 505                 510

Cys Val Leu His Ser Ile Cys Ser Arg Arg Asp Ala Cys Glu Arg Ala
```

```
                515                 520                 525
Asp Glu Pro Gln Arg Phe Ala Asp Leu Leu Gln Cys Val Gln Leu
        530                 535                 540
Thr Val Gln Pro Arg Asn Val Ser Val Thr Met Ser Gln Val Pro Leu
545                 550                 555                 560
Val Leu Gln Ala Trp Asn Val Pro Asp Leu Ser Ala Gly Val Asn Cys
                565                 570                 575
Ser Phe Glu Asp Phe Thr Glu Ser Glu Ser Val Leu Glu Asp Gly Arg
            580                 585                 590
Ile His Cys Arg Ser Pro Ser Ala Arg Glu Val Ala Pro Ile Thr Arg
        595                 600                 605
Gly Gln Gly Asp Gln Arg Val Val Lys Leu Tyr Xaa Lys Ser Lys Glu
    610                 615                 620
Thr Gly Lys Lys Phe Ala Ser Val Asp Phe Val Phe Tyr Asn Cys Ser
625                 630                 635                 640
Val His Gln Ser Cys Leu Ser Cys Val Asn Gly Ser Phe Pro Cys His
                645                 650                 655
Trp Cys Lys Tyr Arg His Val Cys Thr His Asn Val Ala Asp Cys Ala
            660                 665                 670
Phe Leu Glu Gly Arg Val Asn Val Ser Glu Asp Cys Pro Gln Ile Leu
        675                 680                 685
Pro Ser Thr Gln Ile Tyr Val Pro Val Gly Val Val Lys Pro Ile Thr
    690                 695                 700
Leu Ala Ala Arg Asn Leu Pro Gln Pro Gln Ser Gly Gln Arg Gly Tyr
705                 710                 715                 720
Glu Cys Leu Phe His Ile Pro Gly Ser Pro Ala Arg Val Thr Ala Leu
                725                 730                 735
Arg Phe Asn Ser Ser Leu Gln Cys Gln Asn Ser Ser Tyr Ser Tyr
            740                 745                 750
Glu Gly Asn Asp Val Ser Asp Leu Pro Val Asn Leu Ser Val Val Trp
        755                 760                 765
Asn Gly Asn Phe Val Ile Asp Asn Pro Gln Asn Ile Gln Ala His Leu
    770                 775                 780
Tyr Lys Cys Pro Ala Leu Arg Glu Ser Cys Gly Leu Cys Leu Lys Ala
785                 790                 795                 800
Asp Pro Arg Phe Glu Cys Gly Trp Cys Val Ala Glu Arg Arg Cys Ser
                805                 810                 815
Leu Arg His His Cys Ala Ala Asp Thr Pro Ala Ser Trp Met His Ala
            820                 825                 830
Arg His Gly Ser Ser Arg Cys Thr Asp Pro Lys Ile Leu Lys Leu Ser
        835                 840                 845
Pro Glu Thr Gly Pro Arg Gln Gly Gly Thr Arg Leu Thr Ile Thr Gly
    850                 855                 860
Glu Asn Leu Gly Leu Arg Phe Glu Asp Val Arg Leu Gly Val Arg Val
865                 870                 875                 880
Gly Lys Val Leu Cys Ser Pro Val Glu Ser Glu Tyr Ile Ser Ala Glu
                885                 890                 895
Gln Ile Val Cys Glu Ile Gly Asp Ala Ser Ser Val Arg Ala His Asp
            900                 905                 910
Ala Leu Val Glu Val Cys Val Arg Asp Cys Ser Pro His Tyr Arg Ala
        915                 920                 925
Leu Ser Pro Lys Arg Phe Thr Phe Val Thr Pro Thr Phe Tyr Arg Val
    930                 935                 940
```

-continued

```
Ser Pro Ser Arg Gly Pro Leu Ser Gly Gly Thr Trp Ile Gly Ile Glu
945                 950                 955                 960

Gly Ser His Leu Asn Ala Gly Ser Asp Val Ala Val Ser Val Gly Gly
                965                 970                 975

Arg Pro Cys Ser Phe Ser Trp Arg Asn Ser Arg Glu Ile Arg Cys Leu
            980                 985                 990

Thr Pro Pro Gly Gln Ser Pro Gly  Ser Ala Pro Ile Ile  Ile Asn Ile
        995                 1000                1005

Asn Arg  Ala Gln Leu Thr Asn  Pro Glu Val Lys Tyr  Asn Tyr Thr
    1010                 1015                1020

Glu Asp  Pro Thr Ile Leu Arg  Ile Asp Pro Glu Trp  Ser Ile Asn
    1025                 1030                1035

Ser Gly  Gly Thr Leu Leu Thr  Val Thr Gly Thr Asn  Leu Ala Thr
    1040                 1045                1050

Val Arg  Glu Pro Arg Ile Arg  Ala Lys Tyr Gly Gly  Ile Glu Arg
    1055                 1060                1065

Glu Asn  Gly Cys Leu Val Tyr  Asn Asp Thr Thr Met  Val Cys Arg
    1070                 1075                1080

Ala Pro  Ser Val Ala Asn Pro  Val Arg Ser Pro Pro  Glu Leu Gly
    1085                 1090                1095

Glu Arg  Pro Asp Glu Leu Gly  Phe Val Met Asp Asn  Val Arg Ser
    1100                 1105                1110

Leu Leu  Val Leu Asn Ser Thr  Ser Phe Leu Tyr Tyr  Pro Asp Pro
    1115                 1120                1125

Val Leu  Glu Pro Leu Ser Pro  Thr Gly Leu Leu Glu  Leu Lys Pro
    1130                 1135                1140

Ser Ser  Pro Leu Ile Leu Lys  Gly Arg Asn Leu Leu  Pro Pro Ala
    1145                 1150                1155

Pro Gly  Asn Ser Arg Leu Asn  Tyr Thr Val Leu Ile  Gly Ser Thr
    1160                 1165                1170

Pro Cys  Thr Leu Thr Val Ser  Glu Thr Gln Leu Leu  Cys Glu Ala
    1175                 1180                1185

Pro Asn  Leu Thr Gly Gln His  Lys Val Thr Val Arg  Ala Gly Gly
    1190                 1195                1200

Phe Glu  Phe Ser Pro Gly Thr  Leu Gln Val Tyr Ser  Asp Ser Leu
    1205                 1210                1215

Leu Thr  Leu Pro Ala Ile Val  Gly Ile Gly Gly Gly  Gly Gly Leu
    1220                 1225                1230

Leu Leu  Leu Val Ile Val Ala  Val Leu Ile Ala Tyr  Lys Arg Lys
    1235                 1240                1245

Ser Arg  Asp Ala Asp Arg Thr  Leu Lys Arg Leu Gln  Leu Gln Met
    1250                 1255                1260

Asp Asn  Leu Glu Ser Arg Val  Ala Leu Glu Cys Lys  Glu Ala Phe
    1265                 1270                1275

Ala Glu  Leu Gln Thr Asp Ile  His Glu Leu Thr Asn  Asp Leu Asp
    1280                 1285                1290

Gly Ala  Gly Ile Pro Phe Leu  Asp Tyr Arg Thr Tyr  Ala Met Arg
    1295                 1300                1305

Val Leu  Phe Pro Gly Ile Glu  Asp His Pro Val Leu  Lys Glu Met
    1310                 1315                1320

Glu Val  Gln Ala Asn Val Glu  Lys Ser Leu Thr Leu  Phe Gly Gln
    1325                 1330                1335
```

-continued

```
Leu Leu Thr Lys Lys His Phe Leu Leu Thr Phe Ile Arg Thr Leu
1340                1345                1350

Glu Ala Gln Arg Ser Phe Ser Met Arg Asp Arg Gly Asn Val Ala
1355                1360                1365

Ser Leu Ile Met Thr Ala Leu Gln Gly Glu Met Glu Tyr Ala Thr
1370                1375                1380

Gly Val Leu Lys Gln Leu Leu Ser Asp Leu Ile Glu Lys Asn Leu
1385                1390                1395

Glu Ser Lys Asn His Pro Lys Leu Leu Leu Arg Arg Thr Glu Ser
1400                1405                1410

Val Ala Glu Lys Met Leu Thr Asn Trp Phe Thr Phe Leu Leu Tyr
1415                1420                1425

Lys Phe Leu Lys Glu Cys Ala Gly Glu Pro Leu Phe Met Leu Tyr
1430                1435                1440

Cys Ala Ile Lys Gln Gln Met Glu Lys Gly Pro Ile Asp Ala Ile
1445                1450                1455

Thr Gly Glu Ala Arg Tyr Ser Leu Ser Glu Asp Lys Leu Ile Arg
1460                1465                1470

Xaa Gln Ile Asp Tyr Lys Thr Leu Thr Leu Asn Cys Val Asn Pro
1475                1480                1485

Glu Asn Glu Asn Ala Pro Glu Val Pro Val Lys Gly Leu Asp Cys
1490                1495                1500

Asp Thr Val Thr Gln Ala Lys Glu Lys Leu Leu Asp Ala Ala Tyr
1505                1510                1515

Lys Gly Val Pro Tyr Ser Gln Arg Pro Lys Ala Ala Asp Met Asp
1520                1525                1530

Leu Glu Trp Arg Gln Gly Arg Met Ala Arg Ile Ile Leu Gln Asp
1535                1540                1545

Glu Asp Val Thr Thr Lys Ile Asp Asn Asp Trp Lys Arg Leu Asn
1550                1555                1560

Thr Leu Ala His Tyr Gln Val Thr Asp Gly Ser Ser Val Ala Leu
1565                1570                1575

Val Pro Lys Gln Thr Ser Ala Tyr Asn Ile Ser Asn Ser Ser Thr
1580                1585                1590

Phe Thr Lys Ser Leu Ser Arg Tyr Glu Ser Met Leu Arg Thr Ala
1595                1600                1605

Ser Ser Pro Asp Ser Leu Arg Ser Arg Thr Pro Met Ile Thr Pro
1610                1615                1620

Asp Leu Glu Ser Gly Thr Lys Leu Trp His Leu Val Lys Asn His
1625                1630                1635

Asp His Leu Asp Gln Arg Glu Gly Asp Arg Gly Ser Lys Met Val
1640                1645                1650

Ser Glu Ile Tyr Leu Thr Arg Leu Leu Ala Thr Lys Gly Thr Leu
1655                1660                1665

Gln Lys Phe Val Asp Asp Leu Phe Glu Thr Ile Phe Ser Thr Ala
1670                1675                1680

His Arg Gly Ser Ala Leu Pro Leu Ala Ile Lys Tyr Met Phe Asp
1685                1690                1695

Phe Leu Asp Glu Gln Ala Asp Lys His Gln Ile His Asp Ala Asp
1700                1705                1710

Val Arg His Thr Trp Lys Ser Asn Cys Leu Pro Leu Arg Phe Trp
1715                1720                1725

Val Asn Val Ile Lys Asn Pro Gln Phe Val Phe Asp Ile His Lys
```

-continued

```
              1730                1735                1740

Asn Ser  Ile Thr Asp Ala Cys  Leu Ser Val Val
    1745                1750

<210> SEQ ID NO 6
<211> LENGTH: 1894
<212> TYPE: PRT
<213> ORGANISM: Mus musculus

<400> SEQUENCE: 6

Met Pro Leu Pro Pro Leu Ser Ser Arg Thr Leu Leu Leu Leu Leu Leu
1               5                   10                  15

Leu Leu Leu Arg Gly Val Trp Ile Ala Ile Ser Ser Pro Pro Ala Gly
            20                  25                  30

Leu Gly Pro Gln Pro Ala Phe Arg Thr Phe Val Ala Ser Asp Trp Gly
        35                  40                  45

Leu Thr His Leu Val Val His Glu Gln Thr Gly Glu Val Tyr Val Gly
    50                  55                  60

Ala Val Asn Arg Ile Tyr Lys Leu Ser Gly Asn Leu Thr Leu Leu Arg
65                  70                  75                  80

Ala His Val Thr Gly Pro Val Glu Asp Asn Glu Lys Cys Tyr Pro Pro
                85                  90                  95

Pro Ser Val Gln Ser Cys Pro His Gly Leu Gly Ser Thr Asp Asn Val
            100                 105                 110

Asn Lys Leu Leu Leu Leu Asp Tyr Ala Ala Asn Arg Leu Leu Ala Cys
        115                 120                 125

Gly Ser Ala Ser Gln Gly Ile Cys Gln Phe Leu Arg Leu Asp Asp Leu
    130                 135                 140

Phe Lys Leu Gly Glu Pro His His Arg Lys Glu His Tyr Leu Ser Ser
145                 150                 155                 160

Val Arg Glu Ala Gly Ser Met Ala Gly Val Leu Ile Ala Gly Pro Pro
                165                 170                 175

Gly Gln Gly Gln Ala Lys Leu Phe Val Gly Thr Pro Ile Asp Gly Lys
            180                 185                 190

Ser Glu Tyr Phe Pro Thr Leu Ser Ser Arg Arg Leu Met Ala Asn Glu
        195                 200                 205

Glu Asp Ala Asp Met Phe Gly Phe Val Tyr Gln Asp Glu Phe Val Ser
    210                 215                 220

Ser Gln Leu Lys Ile Pro Ser Asp Thr Leu Ser Lys Phe Pro Ala Phe
225                 230                 235                 240

Asp Ile Tyr Tyr Val Tyr Ser Phe Arg Ser Glu Gln Phe Val Tyr Tyr
                245                 250                 255

Leu Thr Leu Gln Leu Asp Thr Gln Leu Thr Ser Pro Asp Ala Ala Gly
            260                 265                 270

Glu His Phe Phe Thr Ser Lys Ile Val Arg Leu Cys Val Asn Asp Pro
        275                 280                 285

Lys Phe Tyr Ser Tyr Val Glu Phe Pro Ile Gly Cys Glu Gln Ala Gly
    290                 295                 300

Val Glu Tyr Arg Leu Val Gln Asp Ala Tyr Leu Ser Arg Pro Gly Gln
305                 310                 315                 320

Ala Leu Ala Lys Gln Leu Gly Leu Ala Glu Asp Glu Val Leu Phe
                325                 330                 335

Thr Val Phe Ala Gln Gly Gln Lys Asn Arg Val Lys Pro Pro Lys Glu
            340                 345                 350
```

-continued

```
Ser Ala Leu Cys Leu Phe Thr Leu Arg Ala Ile Lys Glu Lys Ile Lys
        355                 360                 365
Glu Arg Ile Gln Ser Cys Tyr Arg Gly Glu Gly Lys Leu Ser Leu Pro
    370                 375                 380
Trp Leu Leu Asn Lys Glu Leu Gly Cys Ile Asn Ser Pro Leu Gln Ile
385                 390                 395                 400
Asp Asp Asp Phe Cys Gly Gln Asp Phe Asn Gln Pro Leu Gly Gly Thr
                405                 410                 415
Val Thr Ile Glu Gly Thr Pro Leu Phe Val Asp Lys Glu Asp Gly Leu
            420                 425                 430
Thr Ala Val Ala Ala Tyr Asp Tyr Gln Gly Arg Thr Val Val Phe Ala
        435                 440                 445
Gly Thr Arg Ser Gly Arg Ile Arg Lys Ile Leu Val Asp Leu Ala Asn
    450                 455                 460
Pro Ser Gly Arg Pro Ala Leu Ala Tyr Glu Ser Val Val Ala Gln Glu
465                 470                 475                 480
Gly Asn Pro Ile Leu Arg Asp Leu Val Leu Ser Pro Asn Arg Gln Tyr
                485                 490                 495
Leu Tyr Ala Met Thr Glu Lys Gln Val Thr Gln Val Pro Val Glu Ser
            500                 505                 510
Cys Val Gln Tyr Thr Ser Cys Glu Leu Cys Leu Gly Ser Arg Asp Pro
        515                 520                 525
His Cys Gly Trp Cys Val Leu His Ser Ile Cys Ser Arg Gln Asp Ala
    530                 535                 540
Cys Glu Arg Ala Glu Glu Pro Gln Arg Phe Ala Ser Asp Leu Leu Gln
545                 550                 555                 560
Cys Val Gln Leu Thr Val Gln Pro Arg Asn Val Ser Val Thr Met Ser
                565                 570                 575
Gln Val Pro Leu Val Leu Gln Ala Trp Asn Val Pro Asp Leu Ser Ala
            580                 585                 590
Gly Val Asn Cys Ser Phe Glu Asp Phe Thr Glu Thr Glu Ser Ile Leu
        595                 600                 605
Glu Asp Gly Arg Ile His Cys His Ser Pro Ser Ala Arg Glu Val Ala
    610                 615                 620
Pro Ile Thr Gln Gly Gln Gly Asp Gln Arg Val Val Lys Leu Tyr Leu
625                 630                 635                 640
Lys Ser Lys Glu Thr Gly Lys Lys Phe Ala Ser Val Asp Phe Val Phe
                645                 650                 655
Tyr Asn Cys Ser Val His Gln Ser Cys Leu Ala Cys Val Asn Gly Ser
            660                 665                 670
Phe Pro Cys His Trp Cys Lys Tyr Arg His Val Cys Thr Asn Asn Ala
        675                 680                 685
Ala Asp Cys Ala Phe Leu Glu Gly Arg Val Asn Met Ser Glu Asp Cys
    690                 695                 700
Pro Gln Ile Leu Pro Ser Thr His Ile Tyr Val Pro Val Gly Val Val
705                 710                 715                 720
Lys Pro Ile Thr Leu Ala Ala Arg Asn Leu Pro Gln Pro Gln Ser Gly
                725                 730                 735
Gln Arg Gly Tyr Glu Cys Leu Phe His Ile Pro Gly Ser Pro Ala Arg
            740                 745                 750
Val Thr Ala Leu Arg Phe Asn Ser Ser Leu Gln Cys Gln Asn Ser
        755                 760                 765
Ser Tyr Ser Tyr Glu Gly Asn Asp Val Ser Asp Leu Pro Val Asn Leu
```

-continued

```
            770                 775                 780
Ser Val Val Trp Asn Gly Asn Phe Val Ile Asp Asn Pro Gln Asn Ile
785                 790                 795                 800

Gln Ala His Leu Tyr Lys Cys Pro Ala Leu Arg Gln Ser Cys Gly Leu
                805                 810                 815

Cys Leu Lys Ala Asp Pro Arg Phe Glu Cys Gly Trp Cys Val Ala Glu
                820                 825                 830

Arg Arg Cys Ser Leu Arg His His Cys Pro Ala Asp Ser Pro Ala Ser
                835                 840                 845

Trp Met His Ala His His Gly Ser Ser Arg Cys Thr Asp Pro Lys Ile
850                 855                 860

Leu Lys Leu Ser Pro Glu Thr Gly Pro Arg Gln Gly Thr Arg Leu
865                 870                 875                 880

Thr Ile Thr Gly Glu Asn Leu Gly Leu Arg Phe Glu Asp Val Arg Leu
                885                 890                 895

Gly Val His Val Gly Lys Val Leu Cys Ser Pro Val Glu Ser Glu Tyr
                900                 905                 910

Ile Ser Ala Glu Gln Ile Val Cys Glu Ile Gly Asp Ala Ser Thr Leu
                915                 920                 925

Arg Ala His Asp Ala Leu Val Glu Val Cys Val Arg Asp Cys Ser Leu
                930                 935                 940

His Tyr Arg Ala Leu Ser Pro Lys Arg Phe Thr Phe Val Thr Pro Thr
945                 950                 955                 960

Phe Tyr Arg Val Ser Pro Ser Arg Gly Pro Leu Ser Gly Gly Thr Trp
                965                 970                 975

Ile Gly Ile Glu Gly Ser His Leu Asn Ala Gly Ser Asp Val Ala Val
                980                 985                 990

Ser Ile Gly Gly Arg Pro Cys Ser  Phe Ser Trp Arg Asn  Ser Arg Glu
                995                1000                1005

Ile Arg Cys Leu Thr Pro  Gly His Thr Pro  Gly Ser Ala Pro
1010                1015                1020

Ile Val  Ile Asn Ile Asn Arg  Ala Gln Leu Ser Asn  Pro Glu Val
1025                1030                1035

Lys Tyr  Asn Tyr Thr Glu Asp  Pro Thr Ile Leu Arg  Ile Asp Pro
1040                1045                1050

Glu Trp  Ser Ile Asn Ser Gly  Gly Thr Leu Leu Thr  Val Thr Gly
1055                1060                1065

Thr Asn  Leu Ala Thr Val Arg  Glu Pro Arg Ile Arg  Ala Lys Tyr
1070                1075                1080

Gly Gly  Ile Glu Arg Glu Asn  Ser Cys Met Val Tyr  Asn Asp Thr
1085                1090                1095

Thr Met  Val Cys Arg Ala Pro  Ser Ile Asp Asn Pro  Lys Arg Ser
1100                1105                1110

Pro Pro  Glu Leu Gly Glu Arg  Pro Asp Glu Ile Gly  Phe Ile Met
1115                1120                1125

Asp Asn  Val Arg Thr Leu Leu  Val Leu Asn Ser Ser  Ser Phe Leu
1130                1135                1140

Tyr Tyr  Pro Asp Pro Val Leu  Glu Pro Leu Ser Pro  Thr Gly Leu
1145                1150                1155

Leu Glu  Leu Lys Pro Ser Ser  Pro Leu Ile Leu Lys  Gly Arg Asn
1160                1165                1170

Leu Leu  Pro Pro Ala Pro Gly  Asn Ser Arg Leu Asn  Tyr Thr Val
1175                1180                1185
```

-continued

```
Leu Ile Gly Ser Thr Pro Cys Ile Leu Thr Val Ser Glu Thr Gln
    1190                1195                1200

Leu Leu Cys Glu Ala Pro Asn Leu Thr Gly Gln His Lys Val Thr
    1205                1210                1215

Val Arg Ala Gly Gly Phe Glu Phe Ser Pro Gly Met Leu Gln Val
    1220                1225                1230

Tyr Ser Asp Ser Leu Leu Thr Leu Pro Ala Ile Val Gly Ile Gly
    1235                1240                1245

Gly Gly Gly Gly Leu Leu Leu Val Ile Val Ala Val Leu Ile
    1250                1255                1260

Ala Tyr Lys Arg Lys Ser Arg Asp Ala Asp Arg Thr Leu Lys Arg
    1265                1270                1275

Leu Gln Leu Gln Met Asp Asn Leu Glu Ser Arg Val Ala Leu Glu
    1280                1285                1290

Cys Lys Glu Ala Phe Ala Glu Leu Gln Thr Asp Ile His Glu Leu
    1295                1300                1305

Thr Ser Asp Leu Asp Gly Ala Gly Ile Pro Phe Leu Asp Tyr Arg
    1310                1315                1320

Thr Tyr Ala Met Arg Val Leu Phe Pro Gly Ile Glu Asp His Pro
    1325                1330                1335

Val Leu Lys Glu Met Glu Val Gln Ala Asn Val Glu Lys Ser Leu
    1340                1345                1350

Thr Leu Phe Gly Gln Leu Leu Thr Lys Lys His Phe Leu Leu Thr
    1355                1360                1365

Phe Ile Arg Thr Leu Glu Ala Gln Arg Ser Phe Ser Met Arg Asp
    1370                1375                1380

Arg Gly Asn Val Ala Ser Leu Ile Met Thr Ala Leu Gln Gly Glu
    1385                1390                1395

Met Glu Tyr Ala Thr Gly Val Leu Lys Gln Leu Leu Ser Asp Leu
    1400                1405                1410

Ile Glu Lys Asn Leu Glu Ser Lys Asn His Pro Lys Leu Leu Leu
    1415                1420                1425

Arg Arg Thr Glu Ser Val Ala Glu Lys Met Leu Thr Asn Trp Phe
    1430                1435                1440

Thr Phe Leu Leu Tyr Lys Phe Leu Lys Glu Cys Ala Gly Glu Pro
    1445                1450                1455

Leu Phe Met Leu Tyr Cys Ala Ile Lys Gln Gln Met Glu Lys Gly
    1460                1465                1470

Pro Ile Asp Ala Ile Thr Gly Glu Ala Arg Tyr Ser Leu Ser Glu
    1475                1480                1485

Asp Lys Leu Ile Arg Gln Gln Ile Asp Tyr Lys Thr Leu Thr Leu
    1490                1495                1500

Asn Cys Val Asn Pro Glu His Glu Asn Ala Pro Glu Val Pro Val
    1505                1510                1515

Lys Gly Leu Asn Cys Asp Thr Val Thr Gln Val Lys Glu Lys Leu
    1520                1525                1530

Leu Asp Ala Val Tyr Lys Gly Val Pro Tyr Ser Gln Arg Pro Lys
    1535                1540                1545

Ala Gly Asp Met Asp Leu Glu Trp Arg Gln Gly Arg Met Ala Arg
    1550                1555                1560

Ile Ile Leu Gln Asp Glu Asp Val Thr Thr Lys Ile Asp Asn Asp
    1565                1570                1575
```

```
Trp Lys Arg Leu Asn Thr Leu Ala His Tyr Gln Val Thr Asp Gly
1580            1585                1590

Ser Ser Val Ala Leu Val Pro Lys Gln Thr Ser Ala Tyr Asn Ile
1595            1600                1605

Ser Asn Ser Ser Thr Phe Thr Lys Ser Leu Ser Arg Tyr Glu Ser
1610            1615                1620

Met Leu Arg Thr Ala Ser Ser Pro Asp Ser Leu Arg Ser Arg Thr
1625            1630                1635

Pro Met Ile Thr Pro Asp Leu Glu Ser Gly Thr Lys Leu Trp His
1640            1645                1650

Leu Val Lys Asn His Asp His Leu Asp Gln Arg Glu Gly Asp Arg
1655            1660                1665

Gly Ser Lys Met Val Ser Glu Ile Tyr Leu Thr Arg Leu Leu Ala
1670            1675                1680

Thr Lys Gly Thr Leu Gln Lys Phe Val Asp Asp Leu Phe Glu Thr
1685            1690                1695

Ile Phe Ser Thr Ala His Arg Gly Ser Ala Leu Pro Leu Ala Ile
1700            1705                1710

Lys Tyr Met Phe Asp Phe Leu Asp Glu Gln Ala Asp Lys His Gln
1715            1720                1725

Ile His Asp Ser Asp Val Arg His Thr Trp Lys Ser Asn Cys Leu
1730            1735                1740

Pro Leu Arg Phe Trp Val Asn Val Ile Lys Asn Pro Gln Phe Val
1745            1750                1755

Phe Asp Ile His Lys Asn Ser Ile Thr Asp Ala Cys Leu Ser Val
1760            1765                1770

Val Ala Gln Thr Phe Met Asp Ser Cys Ser Thr Ser Glu His Lys
1775            1780                1785

Leu Gly Lys Asp Ser Pro Ser Asn Lys Leu Leu Tyr Ala Lys Asp
1790            1795                1800

Ile Pro Asn Tyr Lys Ser Trp Val Glu Arg Tyr Tyr Ala Asp Ile
1805            1810                1815

Ala Lys Met Pro Ala Ile Ser Asp Gln Asp Met Ser Ala Tyr Leu
1820            1825                1830

Ala Glu Gln Ser Arg Leu His Leu Ser Gln Phe Asn Ser Met Ser
1835            1840                1845

Ala Leu His Glu Ile Tyr Ser Tyr Ile Ala Lys Tyr Lys Asp Glu
1850            1855                1860

Ile Leu Val Ala Leu Glu Lys Asp Glu Gln Ala Arg Arg Gln Arg
1865            1870                1875

Leu Arg Ser Lys Leu Glu Gln Val Val Asp Thr Met Ala Leu Ser
1880            1885                1890

Ser

<210> SEQ ID NO 7
<211> LENGTH: 930
<212> TYPE: PRT
<213> ORGANISM: Homo sapiens

<400> SEQUENCE: 7

Met Pro Arg Ala Pro His Phe Met Pro Leu Leu Leu Leu Leu Leu
1               5                   10                  15

Leu Ser Leu Pro His Thr Gln Ala Ala Phe Pro Gln Asp Pro Leu
                20                  25                  30
```

-continued

```
Leu Leu Ile Ser Asp Leu Gln Gly Thr Ser Pro Leu Ser Trp Phe Arg
         35                  40                  45

Gly Leu Glu Asp Asp Ala Val Ala Ala Glu Leu Gly Leu Asp Phe Gln
 50                  55                  60

Arg Phe Leu Thr Leu Asn Arg Thr Leu Leu Val Ala Ala Arg Asp His
 65                  70                  75                  80

Val Phe Ser Phe Asp Leu Gln Ala Glu Glu Gly Glu Gly Leu Val
                 85                  90                  95

Pro Asn Lys Tyr Leu Thr Trp Arg Ser Gln Asp Val Glu Asn Cys Ala
                100                 105                 110

Val Arg Gly Lys Leu Thr Asp Glu Cys Tyr Asn Tyr Ile Arg Val Leu
                115                 120                 125

Val Pro Trp Asp Ser Gln Thr Leu Leu Ala Cys Gly Thr Asn Ser Phe
            130                 135                 140

Ser Pro Val Cys Arg Ser Tyr Gly Ile Thr Ser Leu Gln Gln Glu Gly
145                 150                 155                 160

Glu Glu Leu Ser Gly Gln Ala Arg Cys Pro Phe Asp Ala Thr Gln Ser
                165                 170                 175

Asn Val Ala Ile Phe Ala Glu Gly Ser Leu Tyr Ser Ala Thr Ala Ala
                180                 185                 190

Asp Phe Gln Ala Ser Asp Ala Val Val Tyr Arg Ser Leu Gly Pro Gln
            195                 200                 205

Pro Pro Leu Arg Ser Ala Lys Tyr Asp Ser Lys Trp Leu Arg Glu Pro
210                 215                 220

His Phe Val Gln Ala Leu Glu His Gly Asp His Val Tyr Phe Phe Phe
225                 230                 235                 240

Arg Glu Val Ser Val Glu Asp Ala Arg Leu Gly Lys Val Gln Phe Ser
                245                 250                 255

Arg Val Ala Arg Val Cys Lys Arg Asp Met Gly Gly Ser Pro Arg Ala
                260                 265                 270

Leu Asp Arg His Trp Thr Ser Phe Leu Lys Leu Arg Leu Asn Cys Ser
            275                 280                 285

Val Pro Gly Asp Ser Thr Phe Tyr Phe Asp Val Leu Gln Ala Leu Thr
290                 295                 300

Gly Pro Val Asn Leu His Gly Arg Ser Ala Leu Phe Gly Val Phe Thr
305                 310                 315                 320

Thr Gln Thr Asn Ser Ile Pro Gly Ser Ala Val Cys Ala Phe Tyr Leu
                325                 330                 335

Asp Glu Ile Glu Arg Gly Phe Glu Gly Lys Phe Lys Glu Gln Arg Ser
                340                 345                 350

Leu Asp Gly Ala Trp Thr Pro Val Ser Glu Asp Arg Val Pro Ser Pro
            355                 360                 365

Arg Pro Gly Ser Cys Ala Gly Val Gly Ala Ala Leu Phe Ser Ser
370                 375                 380

Ser Arg Asp Leu Pro Asp Asp Val Leu Thr Phe Ile Lys Ala His Pro
385                 390                 395                 400

Leu Leu Asp Pro Ala Val Pro Val Thr His Gln Pro Leu Leu Thr
                405                 410                 415

Leu Thr Ser Arg Ala Leu Leu Thr Gln Val Ala Val Asp Gly Met Ala
            420                 425                 430

Gly Pro His Ser Asn Ile Thr Val Met Phe Leu Gly Ser Asn Asp Gly
                435                 440                 445

Thr Val Leu Lys Val Leu Thr Pro Gly Gly Arg Ser Gly Gly Pro Glu
```

-continued

```
        450                 455                 460
Pro Ile Leu Leu Glu Glu Ile Asp Ala Tyr Ser Pro Ala Arg Cys Ser
465                 470                 475                 480

Gly Lys Arg Thr Ala Gln Thr Ala Arg Ile Ile Gly Leu Glu Leu
                485                 490                 495

Asp Thr Glu Gly His Arg Leu Phe Val Ala Phe Ser Gly Cys Ile Val
            500                 505                 510

Tyr Leu Pro Leu Ser Arg Cys Ala Arg His Gly Ala Cys Gln Arg Ser
            515                 520                 525

Cys Leu Ala Ser Gln Asp Pro Tyr Cys Gly Trp His Ser Ser Arg Gly
530                 535                 540

Cys Val Asp Ile Arg Gly Ser Gly Thr Asp Val Asp Gln Ala Gly
545                 550                 555                 560

Asn Gln Glu Ser Met Glu His Gly Asp Cys Gln Asp Gly Ala Thr Gly
                565                 570                 575

Ser Gln Ser Gly Pro Gly Asp Ser Ala Tyr Gly Val Arg Arg Asp Leu
            580                 585                 590

Pro Pro Ala Ser Ala Ser Arg Ser Val Pro Ile Pro Leu Leu Leu Ala
            595                 600                 605

Ser Val Ala Ala Ala Phe Ala Leu Gly Ala Ser Val Ser Gly Leu Leu
        610                 615                 620

Val Ser Cys Ala Cys Arg Arg Ala His Arg Arg Gly Lys Asp Ile
625                 630                 635                 640

Glu Thr Pro Gly Leu Pro Arg Pro Leu Ser Leu Arg Ser Leu Ala Arg
                645                 650                 655

Leu His Gly Gly Gly Pro Glu Pro Pro Pro Ser Lys Asp Gly Asp
            660                 665                 670

Ala Val Gln Thr Pro Gln Leu Tyr Thr Thr Phe Leu Pro Pro Pro Glu
            675                 680                 685

Gly Val Pro Pro Glu Leu Ala Cys Leu Pro Thr Pro Glu Ser Thr
        690                 695                 700

Pro Glu Leu Pro Val Lys His Leu Arg Ala Ala Gly Asp Pro Trp Glu
705                 710                 715                 720

Trp Asn Gln Asn Arg Asn Asn Ala Lys Glu Gly Pro Gly Arg Ser Arg
                725                 730                 735

Gly Gly His Ala Ala Gly Gly Pro Ala Pro Arg Val Leu Val Arg Pro
            740                 745                 750

Pro Pro Pro Gly Cys Pro Gly Gln Ala Val Glu Val Thr Thr Leu Glu
            755                 760                 765

Glu Leu Leu Arg Tyr Leu His Gly Pro Gln Pro Pro Arg Lys Gly Ala
        770                 775                 780

Glu Pro Pro Ala Pro Leu Thr Ser Arg Ala Leu Pro Glu Pro Ala
785                 790                 795                 800

Pro Ala Leu Leu Gly Gly Pro Ser Pro Arg Pro His Glu Cys Ala Ser
                805                 810                 815

Pro Leu Arg Leu Asp Val Pro Pro Glu Gly Arg Cys Ala Ser Ala Pro
            820                 825                 830

Ala Arg Pro Ala Leu Ser Ala Pro Ala Pro Arg Leu Gly Val Gly Gly
            835                 840                 845

Gly Arg Arg Leu Pro Phe Ser Gly His Arg Ala Pro Pro Ala Leu Leu
        850                 855                 860

Thr Arg Val Pro Ser Gly Gly Pro Ser Arg Tyr Ser Gly Gly Pro Gly
865                 870                 875                 880
```

```
Lys His Leu Leu Tyr Leu Gly Arg Pro Glu Gly Tyr Arg Gly Arg Ala
            885                 890                 895
Leu Lys Arg Val Asp Val Glu Lys Pro Gln Leu Ser Leu Lys Pro Pro
            900                 905                 910
Leu Val Gly Pro Ser Ser Arg Gln Ala Val Pro Asn Gly Gly Arg Phe
            915                 920                 925
Asn Phe
    930

<210> SEQ ID NO 8
<211> LENGTH: 960
<212> TYPE: PRT
<213> ORGANISM: Rattus norvegicus

<400> SEQUENCE: 8

Met Pro Arg Ala Pro His Ser Met Pro Leu Leu Leu Leu Leu Leu Leu
1               5                   10                  15
Ser Leu Pro Gln Ala Gln Thr Ala Phe Pro Gln Asp Pro Ile Pro Leu
            20                  25                  30
Leu Thr Ser Asp Leu Gln Gly Thr Ser Pro Ser Ser Trp Phe Arg Gly
            35                  40                  45
Leu Glu Asp Asp Ala Val Ala Ala Glu Leu Gly Leu Asp Phe Gln Arg
        50                  55                  60
Phe Leu Thr Leu Asn Arg Thr Leu Leu Val Ala Ala Arg Asp His Val
65              70                  75                  80
Phe Ser Phe Asp Leu Gln Ala Gln Glu Glu Gly Glu Gly Leu Val Pro
                85                  90                  95
Asn Lys Phe Leu Thr Trp Arg Ser Gln Asp Met Glu Asn Cys Ala Val
            100                 105                 110
Arg Gly Lys Leu Thr Asp Glu Cys Tyr Asn Tyr Ile Arg Val Leu Val
            115                 120                 125
Pro Trp Asp Ser Gln Thr Leu Leu Ala Cys Gly Thr Asn Ser Phe Ser
        130                 135                 140
Pro Val Cys Arg Ser Tyr Gly Ile Thr Ser Leu Gln Gln Glu Gly Glu
145             150                 155                 160
Glu Leu Ser Gly Gln Ala Arg Cys Pro Phe Asp Ala Thr Gln Ser Thr
                165                 170                 175
Val Ala Ile Ser Ala Glu Gly Ser Leu Tyr Ser Ala Thr Ala Ala Asp
            180                 185                 190
Phe Gln Ala Ser Asp Ala Val Val Tyr Arg Ser Leu Gly Pro Gln Pro
        195                 200                 205
Pro Leu Arg Ser Ala Lys Tyr Asp Ser Lys Trp Leu Arg Glu Pro His
    210                 215                 220
Phe Val Tyr Ala Leu Glu His Gly Asp His Val Tyr Phe Phe Phe Arg
225             230                 235                 240
Glu Val Ser Val Glu Asp Ala Arg Leu Gly Arg Val Gln Phe Ser Arg
                245                 250                 255
Val Ala Arg Val Cys Lys Arg Asp Met Gly Gly Ser Pro Arg Ala Leu
            260                 265                 270
Asp Arg His Trp Thr Ser Phe Leu Lys Leu Arg Leu Asn Cys Ser Val
        275                 280                 285
Pro Gly Asp Ser Thr Phe Tyr Phe Asp Val Leu Gln Ser Leu Thr Gly
    290                 295                 300
Pro Val Asn Leu His Gly Arg Ser Ala Leu Phe Gly Val Phe Thr Thr
```

-continued

```
            305                 310                 315                 320
        Gln Thr Asn Ser Ile Pro Gly Ser Ala Val Cys Ala Phe Tyr Leu Asp
                        325                 330                 335
        Asp Ile Glu Arg Gly Phe Glu Gly Lys Phe Lys Glu Gln Arg Ser Leu
                        340                 345                 350
        Asp Gly Ala Trp Thr Pro Val Ser Glu Asp Lys Val Pro Ser Pro Arg
                        355                 360                 365
        Pro Gly Ser Cys Ala Gly Val Gly Ala Ala Ala Leu Phe Ser Ser Ser
                        370                 375                 380
        Gln Asp Leu Pro Asp Val Leu Leu Phe Ile Lys Ala His Pro Leu
        385                 390                 395                 400
        Leu Asp Pro Ala Val Pro Pro Ala Thr His Gln Pro Leu Leu Thr Leu
                        405                 410                 415
        Thr Ser Arg Ala Leu Leu Thr Gln Val Ala Val Asp Gly Met Ala Gly
                        420                 425                 430
        Pro His Arg Asn Thr Thr Val Leu Phe Leu Gly Ser Asn Asp Gly Thr
                        435                 440                 445
        Val Leu Lys Val Leu Pro Pro Gly Gly Gln Ser Leu Gly Pro Glu Pro
        450                 455                 460
        Ile Ile Leu Glu Glu Ile Asp Ala Tyr Ser His Ala Arg Cys Ser Gly
        465                 470                 475                 480
        Lys Arg Ser Pro Arg Ala Ala Arg Arg Ile Ile Gly Leu Glu Leu Asp
                        485                 490                 495
        Thr Glu Gly His Arg Leu Phe Val Ala Phe Pro Gly Cys Ile Val Tyr
                        500                 505                 510
        Leu Ser Leu Ser Arg Cys Ala Arg His Gly Ala Cys Gln Arg Ser Cys
                        515                 520                 525
        Leu Ala Ser Leu Asp Pro Tyr Cys Gly Trp His Arg Phe Arg Gly Cys
                        530                 535                 540
        Val Asn Ile Arg Gly Pro Gly Thr Asp Val Asp Leu Thr Gly Asn
        545                 550                 555                 560
        Gln Glu Ser Met Glu His Gly Asp Cys Gln Asp Gly Ala Thr Gly Ser
                        565                 570                 575
        Gln Ser Gly Pro Gly Asp Ser Ala Tyr Val Leu Leu Gly Pro Gly Pro
                        580                 585                 590
        Ser Pro Glu Thr Pro Ser Ser Pro Ser Asp Ala His Pro Gly Pro Gln
                        595                 600                 605
        Ser Ser Thr Leu Gly Ala His Thr Gln Gly Val Arg Arg Asp Leu Ser
                        610                 615                 620
        Pro Ala Ser Ala Ser Arg Ser Ile Pro Ile Pro Leu Leu Ala Cys
        625                 630                 635                 640
        Val Ala Ala Ala Phe Ala Leu Gly Ala Ser Val Ser Gly Leu Leu Val
                        645                 650                 655
        Ser Cys Ala Cys Arg Arg Ala Asn Arg Arg Ser Lys Asp Ile Glu
                        660                 665                 670
        Thr Pro Gly Leu Pro Arg Pro Leu Ser Leu Arg Ser Leu Ala Arg Leu
                        675                 680                 685
        His Gly Gly Gly Pro Glu Pro Pro Pro Lys Asp Gly Asp Ala
                        690                 695                 700
        Ala Gln Thr Pro Gln Leu Tyr Thr Thr Phe Leu Pro Pro Glu Gly
        705                 710                 715                 720
        Gly Ser Pro Pro Glu Leu Ala Cys Leu Pro Thr Pro Glu Thr Thr Pro
                        725                 730                 735
```

```
Glu Leu Pro Val Lys His Leu Arg Ala Ser Gly Gly Pro Trp Glu Trp
                740                 745                 750

Asn Gln Asn Gly Asn Asn Ala Ser Glu Gly Pro Gly Arg Pro Arg Gly
            755                 760                 765

Cys Ser Ala Ala Gly Gly Pro Ala Pro Arg Val Leu Val Arg Pro Pro
770                 775                 780

Pro Pro Gly Cys Pro Gly Gln Glu Val Glu Val Thr Thr Leu Glu Glu
785                 790                 795                 800

Leu Leu Arg Tyr Leu His Gly Pro Gln Pro Pro Arg Lys Gly Ser Glu
                805                 810                 815

Pro Leu Ala Ser Ala Pro Phe Thr Ser Arg Pro Ala Ser Glu Pro
                820                 825                 830

Gly Ala Ala Leu Phe Val Asp Ser Pro Met Pro Arg Asp Cys Val
                835                 840                 845

Pro Pro Leu Arg Leu Asp Val Pro Pro Asp Gly Lys Arg Ala Ala Pro
850                 855                 860

Ser Gly Arg Pro Ala Leu Ser Ala Pro Ala Pro Arg Leu Gly Val Ser
865                 870                 875                 880

Gly Ser Arg Arg Leu Pro Phe Pro Thr His Arg Ala Pro Pro Gly Leu
                885                 890                 895

Leu Thr Arg Val Pro Ser Gly Gly Pro Ser Arg Tyr Ser Gly Gly Pro
                900                 905                 910

Gly Arg His Leu Leu Tyr Leu Gly Arg Pro Asp Gly His Arg Gly Arg
                915                 920                 925

Ser Leu Lys Arg Val Asp Val Lys Ser Pro Leu Ser Pro Lys Pro Pro
                930                 935                 940

Leu Ala Thr Pro Pro Gln Pro Ala Pro His Gly Ser His Phe Asn Phe
945                 950                 955                 960

<210> SEQ ID NO 9
<211> LENGTH: 928
<212> TYPE: PRT
<213> ORGANISM: Rattus norvegicus

<400> SEQUENCE: 9

Met Pro Arg Ala Pro His Ser Met Pro Leu Leu Leu Leu Leu Leu Leu
1               5                   10                  15

Ser Leu Pro Gln Ala Gln Thr Ala Phe Pro Gln Asp Pro Ile Pro Leu
                20                  25                  30

Leu Thr Ser Asp Leu Gln Gly Thr Ser Pro Ser Ser Trp Phe Arg Gly
            35                  40                  45

Leu Glu Asp Asp Ala Val Ala Ala Glu Leu Gly Leu Asp Phe Gln Arg
        50                  55                  60

Phe Leu Thr Leu Asn Arg Thr Leu Leu Val Ala Ala Arg Asp His Val
65                  70                  75                  80

Phe Ser Phe Asp Leu Gln Ala Gln Glu Glu Gly Glu Gly Leu Val Pro
                85                  90                  95

Asn Lys Phe Leu Thr Trp Arg Ser Gln Asp Met Glu Asn Cys Ala Val
            100                 105                 110

Arg Gly Lys Leu Thr Asp Glu Cys Tyr Asn Tyr Ile Arg Val Leu Val
        115                 120                 125

Pro Trp Asp Ser Gln Thr Leu Leu Ala Cys Gly Thr Asn Ser Phe Ser
130                 135                 140

Pro Val Cys Arg Ser Tyr Gly Ile Thr Ser Leu Gln Gln Glu Gly Glu
```

```
            145                 150                 155                 160
Glu Leu Ser Gly Gln Ala Arg Cys Pro Phe Asp Ala Thr Gln Ser Thr
                165                 170                 175
Val Ala Ile Ser Ala Glu Gly Ser Leu Tyr Ser Ala Thr Ala Ala Asp
            180                 185                 190
Phe Gln Ala Ser Asp Ala Val Val Tyr Arg Ser Leu Gly Pro Gln Pro
        195                 200                 205
Pro Leu Arg Ser Ala Lys Tyr Asp Ser Lys Trp Leu Arg Glu Pro His
    210                 215                 220
Phe Val Tyr Ala Leu Glu His Gly Asp His Val Tyr Phe Phe Phe Arg
225                 230                 235                 240
Glu Val Ser Val Glu Asp Ala Arg Leu Gly Arg Val Gln Phe Ser Arg
                245                 250                 255
Val Ala Arg Val Cys Lys Arg Asp Met Gly Gly Ser Pro Arg Ala Leu
            260                 265                 270
Asp Arg His Trp Thr Ser Phe Leu Lys Leu Arg Leu Asn Cys Ser Val
        275                 280                 285
Pro Gly Asp Ser Thr Phe Tyr Phe Asp Val Leu Gln Ser Leu Thr Gly
    290                 295                 300
Pro Val Asn Leu His Gly Arg Ser Ala Leu Phe Gly Val Phe Thr Thr
305                 310                 315                 320
Gln Thr Asn Ser Ile Pro Gly Ser Ala Val Cys Ala Phe Tyr Leu Asp
                325                 330                 335
Asp Ile Glu Arg Gly Phe Glu Gly Lys Phe Lys Glu Gln Arg Ser Leu
            340                 345                 350
Asp Gly Ala Trp Thr Pro Val Ser Glu Asp Lys Val Pro Ser Pro Arg
        355                 360                 365
Pro Gly Ser Cys Ala Gly Val Gly Ala Ala Ala Leu Phe Ser Ser Ser
    370                 375                 380
Gln Asp Leu Pro Asp Asp Val Leu Leu Phe Ile Lys Ala His Pro Leu
385                 390                 395                 400
Leu Asp Pro Ala Val Pro Pro Ala Thr His Gln Pro Leu Leu Thr Leu
                405                 410                 415
Thr Ser Arg Ala Leu Leu Thr Gln Val Ala Val Asp Gly Met Ala Gly
            420                 425                 430
Pro His Arg Asn Thr Thr Val Leu Phe Leu Gly Ser Asn Asp Gly Thr
        435                 440                 445
Val Leu Lys Val Leu Pro Pro Gly Gly Gln Ser Leu Gly Pro Glu Pro
    450                 455                 460
Ile Ile Leu Glu Glu Ile Asp Ala Tyr Ser His Ala Arg Cys Ser Gly
465                 470                 475                 480
Lys Arg Ser Pro Arg Ala Ala Arg Ile Ile Gly Leu Glu Leu Asp
                485                 490                 495
Thr Glu Gly His Arg Leu Phe Val Ala Phe Pro Gly Cys Ile Val Tyr
            500                 505                 510
Leu Ser Leu Ser Arg Cys Ala Arg His Gly Ala Cys Gln Arg Ser Cys
        515                 520                 525
Leu Ala Ser Leu Asp Pro Tyr Cys Gly Trp His Arg Phe Arg Gly Cys
    530                 535                 540
Val Asn Ile Arg Gly Pro Gly Thr Asp Val Asp Leu Thr Gly Asn
545                 550                 555                 560
Gln Glu Ser Met Glu His Gly Asp Cys Gln Asp Gly Ala Thr Gly Ser
                565                 570                 575
```

```
Gln Ser Gly Pro Gly Asp Ser Ala Tyr Gly Val Arg Arg Asp Leu Ser
            580                 585                 590
Pro Ala Ser Ala Ser Arg Ser Ile Pro Ile Pro Leu Leu Leu Ala Cys
            595                 600                 605
Val Ala Ala Ala Phe Ala Leu Gly Ala Ser Val Ser Gly Leu Leu Val
            610                 615                 620
Ser Cys Ala Cys Arg Arg Ala Asn Arg Arg Ser Lys Asp Ile Glu
625                 630                 635                 640
Thr Pro Gly Leu Pro Arg Pro Leu Ser Leu Arg Ser Leu Ala Arg Leu
                    645                 650                 655
His Gly Gly Gly Pro Glu Pro Pro Pro Lys Asp Gly Asp Ala
                    660                 665                 670
Ala Gln Thr Pro Gln Leu Tyr Thr Thr Phe Leu Pro Pro Glu Gly
                    675                 680                 685
Gly Ser Pro Pro Glu Leu Ala Cys Leu Pro Thr Pro Glu Thr Thr Pro
            690                 695                 700
Glu Leu Pro Val Lys His Leu Arg Ala Ser Gly Gly Pro Trp Glu Trp
705                 710                 715                 720
Asn Gln Asn Gly Asn Asn Ala Ser Glu Gly Pro Gly Arg Pro Arg Gly
                    725                 730                 735
Cys Ser Ala Ala Gly Gly Pro Ala Pro Arg Val Leu Val Arg Pro Pro
                    740                 745                 750
Pro Pro Gly Cys Pro Gly Gln Glu Val Glu Val Thr Thr Leu Glu Glu
            755                 760                 765
Leu Leu Arg Tyr Leu His Gly Pro Gln Pro Pro Arg Lys Gly Ser Glu
            770                 775                 780
Pro Leu Ala Ser Ala Pro Phe Thr Ser Arg Pro Ala Ser Glu Pro
785                 790                 795                 800
Gly Ala Ala Leu Phe Val Asp Ser Ser Pro Met Pro Arg Asp Cys Val
                    805                 810                 815
Pro Pro Leu Arg Leu Asp Val Pro Pro Asp Gly Lys Arg Ala Ala Pro
            820                 825                 830
Ser Gly Arg Pro Ala Leu Ser Ala Pro Ala Pro Arg Leu Gly Val Ser
            835                 840                 845
Gly Ser Arg Arg Leu Pro Phe Pro Thr His Arg Ala Pro Pro Gly Leu
            850                 855                 860
Leu Thr Arg Val Pro Ser Gly Gly Pro Ser Arg Tyr Ser Gly Gly Pro
865                 870                 875                 880
Gly Arg His Leu Leu Tyr Leu Gly Arg Pro Asp Gly His Arg Gly Arg
                    885                 890                 895
Ser Leu Lys Arg Val Asp Val Lys Ser Pro Leu Ser Pro Lys Pro Pro
                    900                 905                 910
Leu Ala Thr Pro Pro Gln Pro Ala Pro His Gly Ser His Phe Asn Phe
            915                 920                 925

<210> SEQ ID NO 10
<211> LENGTH: 931
<212> TYPE: PRT
<213> ORGANISM: Mus musculus

<400> SEQUENCE: 10

Met Pro Arg Ala Pro His Ser Met Pro Leu Leu Leu Leu Leu Leu
1               5                   10                  15
Leu Ser Ser Leu Pro Gln Ala Gln Ala Ala Phe Pro Gln Asp Pro Thr
```

-continued

```
                    20                  25                  30
Pro Leu Leu Thr Ser Asp Leu Gln Gly Ala Ser Pro Ser Trp Phe
                35                  40                  45
Arg Gly Leu Glu Asp Asp Ala Val Ala Ala Glu Leu Gly Leu Asp Phe
 50                  55                  60
Gln Arg Phe Leu Thr Leu Asn Arg Thr Leu Leu Val Ala Ala Arg Asp
 65                  70                  75                  80
His Val Phe Ser Phe Asp Leu Gln Ala Gln Glu Glu Gly Glu Gly Leu
                 85                  90                  95
Val Pro Asn Lys Phe Leu Thr Trp Arg Ser Gln Asp Met Glu Asn Cys
            100                 105                 110
Ala Val Arg Gly Lys Leu Thr Asp Glu Cys Tyr Asn Tyr Ile Arg Val
            115                 120                 125
Leu Val Pro Trp Asn Ser Gln Thr Leu Leu Ala Cys Gly Thr Asn Ser
            130                 135                 140
Phe Ser Pro Met Cys Arg Ser Tyr Gly Ile Thr Ser Leu Gln Gln Glu
145                 150                 155                 160
Gly Glu Glu Leu Ser Gly Gln Ala Arg Cys Pro Phe Asp Ala Thr Gln
                165                 170                 175
Ser Thr Val Ala Ile Phe Ala Glu Gly Ser Leu Tyr Ser Ala Thr Ala
                180                 185                 190
Ala Asp Phe Gln Ala Ser Asp Ala Val Val Tyr Arg Ser Leu Gly Pro
            195                 200                 205
Gln Pro Pro Leu Arg Ser Ala Lys Tyr Asp Ser Lys Trp Leu Arg Glu
 210                 215                 220
Pro His Phe Val Tyr Ala Leu Glu His Gly Glu His Val Tyr Phe Phe
225                 230                 235                 240
Phe Arg Glu Val Ser Val Glu Asp Ala Arg Leu Gly Arg Val Gln Phe
                245                 250                 255
Ser Arg Val Ala Arg Val Cys Lys Arg Asp Met Gly Gly Ser Pro Arg
            260                 265                 270
Ala Leu Asp Arg His Trp Thr Ser Phe Leu Lys Leu Arg Leu Asn Cys
            275                 280                 285
Ser Val Pro Gly Asp Ser Thr Phe Tyr Phe Asp Val Leu Gln Ser Leu
 290                 295                 300
Thr Gly Pro Val Asn Leu His Gly Arg Ser Ala Leu Phe Gly Val Phe
305                 310                 315                 320
Thr Thr Gln Thr Asn Ser Ile Pro Gly Ser Ala Val Cys Ala Phe Tyr
                325                 330                 335
Leu Asp Asp Ile Glu Arg Gly Phe Glu Gly Lys Phe Lys Glu Gln Arg
            340                 345                 350
Ser Leu Asp Gly Ala Trp Thr Pro Val Ser Glu Asp Lys Val Pro Ser
            355                 360                 365
Pro Arg Pro Gly Ser Cys Ala Gly Val Gly Ala Ala Ala Ser Phe Ser
            370                 375                 380
Ser Ser Gln Asp Leu Pro Asp Asp Val Leu Leu Phe Ile Lys Ala His
385                 390                 395                 400
Pro Leu Leu Asp Pro Ala Val Pro Pro Ala Thr His Gln Pro Leu Leu
                405                 410                 415
Thr Leu Thr Ser Arg Ala Leu Leu Thr Gln Val Ala Val Asp Gly Met
            420                 425                 430
Ala Gly Pro His Arg Asn Thr Thr Val Leu Phe Leu Gly Ser Asn Asp
            435                 440                 445
```

```
Gly Thr Val Leu Lys Val Leu Pro Pro Gly Gln Ser Leu Gly Ser
    450             455                 460

Glu Pro Ile Val Leu Glu Glu Ile Asp Ala Tyr Ser His Ala Arg Cys
465             470                 475                 480

Ser Gly Lys Arg Ser Pro Arg Ala Ala Arg Ile Ile Gly Leu Glu
            485                 490                 495

Leu Asp Thr Glu Gly His Arg Leu Phe Val Ala Phe Pro Gly Cys Ile
            500                 505                 510

Val Tyr Leu Ser Leu Ser Arg Cys Ala Arg His Gly Ala Cys Gln Arg
            515                 520                 525

Ser Cys Leu Ala Ser Leu Asp Pro Tyr Cys Gly Trp His Arg Ser Arg
    530                 535                 540

Gly Cys Met Ser Ile Arg Gly Pro Gly Gly Thr Asp Val Asp Leu Thr
545                 550                 555                 560

Gly Asn Gln Glu Ser Thr Glu His Gly Asp Cys Gln Asp Gly Ala Thr
                565                 570                 575

Gly Ser Gln Ser Gly Pro Gly Asp Ser Ala Tyr Gly Val Arg Arg Asp
            580                 585                 590

Leu Ser Pro Ala Ser Ala Ser Arg Ser Ile Pro Ile Pro Leu Leu Leu
    595                 600                 605

Ala Cys Val Ala Ala Ala Phe Ala Leu Gly Ala Ser Val Ser Gly Leu
    610                 615                 620

Leu Val Ser Cys Ala Cys Arg Arg Ala Asn Arg Arg Arg Ser Lys Asp
625                 630                 635                 640

Ile Glu Thr Pro Gly Leu Pro Arg Pro Leu Ser Leu Arg Ser Leu Ala
            645                 650                 655

Arg Leu His Gly Gly Pro Glu Pro Pro Pro Pro Lys Asp Gly
            660                 665                 670

Asp Ala Ala Gln Thr Pro Gln Leu Tyr Thr Thr Phe Leu Pro Pro Pro
            675                 680                 685

Asp Gly Gly Ser Pro Pro Glu Leu Ala Cys Leu Pro Thr Pro Glu Thr
    690                 695                 700

Thr Pro Glu Leu Pro Val Lys His Leu Arg Ala Ser Gly Gly Pro Trp
705             710                 715                 720

Glu Trp Asn Gln Asn Gly Asn Asn Ala Ser Glu Gly Pro Gly Arg Pro
            725                 730                 735

Pro Arg Gly Cys Ser Gly Ala Gly Gly Pro Ala Pro Arg Val Leu Val
            740                 745                 750

Arg Pro Pro Pro Gly Cys Pro Gly Gln Ala Val Glu Val Thr Thr
            755                 760                 765

Leu Glu Glu Leu Leu Arg Tyr Leu His Gly Pro Gln Pro Pro Arg Lys
    770                 775                 780

Gly Ser Glu Pro Leu Ala Ser Pro Phe Thr Ser Arg Pro Pro Ala
785                 790                 795                 800

Ser Glu Pro Gly Ala Ser Leu Phe Val Asp Ser Ser Pro Met Pro Arg
                805                 810                 815

Asp Gly Val Pro Pro Leu Arg Leu Asp Val Pro Pro Glu Gly Lys Arg
            820                 825                 830

Ala Ala Pro Ser Gly Arg Pro Ala Leu Ser Ala Pro Ala Pro Arg Leu
            835                 840                 845

Gly Val Gly Gly Ser Arg Arg Leu Pro Phe Pro Thr His Arg Ala Pro
    850                 855                 860
```

-continued

```
Pro Gly Leu Leu Thr Arg Val Pro Ser Gly Gly Pro Ala Arg Tyr Ser
865                 870             875                 880

Gly Gly Pro Gly Arg His Leu Leu Tyr Leu Gly Arg Pro Glu Gly His
                885             890             895

Arg Gly Arg Ser Leu Lys Arg Val Asp Val Lys Ser Pro Leu Ser Pro
            900             905             910

Lys Pro Pro Leu Ala Ser Pro Pro Gln Pro Ala Pro His Gly Gly His
        915             920             925

Phe Asn Phe
    930
```